US005672345A

United States Patent [19]
Curtiss, III

[11] Patent Number: 5,672,345
[45] Date of Patent: Sep. 30, 1997

[54] SELECTIVE MAINTENANCE OF A RECOMBINANT GENE IN A POPULATION OF VACCINE CELLS

[75] Inventor: Roy Curtiss, III, St. Louis, Mo.

[73] Assignee: Washington University, St. Louis, Mo.

[21] Appl. No.: 402,308

[22] Filed: Mar. 10, 1995

Related U.S. Application Data

[63] Continuation of Ser. No. 990,361, Dec. 15, 1992, abandoned, which is a continuation of Ser. No. 251,304, Oct. 3, 1988, abandoned, which is a continuation-in-part of Ser. No. 106,072, Oct. 7, 1987, abandoned.

[51] Int. Cl.$^6$ ................... A61K 39/02; C12P 21/00; C12N 15/00; C12N 1/21
[52] U.S. Cl. ............... 424/93.2; 435/69.1; 435/71.2; 435/172.3; 435/252.3
[58] Field of Search ............... 435/252.3, 172.3, 435/69.1, 71.2; 424/93.2

[56] References Cited

U.S. PATENT DOCUMENTS

| | | | |
|---|---|---|---|
| 4,190,495 | 2/1980 | Curtiss | 435/172.3 |
| 5,294,441 | 3/1994 | Curtiss et al. | 424/200.1 |
| 5,387,744 | 2/1995 | Curtiss et al. | 424/235.1 |

FOREIGN PATENT DOCUMENTS

| | | | |
|---|---|---|---|
| 0080806 | 6/1983 | European Pat. Off. | C12N 15/00 |
| 0 185 512 | 6/1986 | European Pat. Off. | |
| 8503521 | 8/1985 | WIPO | C12N 15/00 |

OTHER PUBLICATIONS

Kaper 1988, Bio/technology vol. 6:633.
Lerner et al. 1983, The Development of Synthetic Vaccines in Dixon et al. Ed. The Biology of Immunologic Disease Sinauer Associates, Massachusetts.
Jacobs et al., 1986, PNAS, vol. 83: 1926–1930.
Ferrari et al., (1985) BioTechnology 3:1003–1007.
Curtiss, (1988) "Engineering Organisms for Safety: What is Necessary" in *Release of Genetically–Engineered Micro–Organisms*, Academic Press, pp. 7–20.
Nakayama et al., (1988) Bio/Technology 6:693–697.
Curtiss et al., (1988) "Recombinant Avirulent Salmonella Vaccine Strains . . . " in *Immunology and Immunopathology of of the Elementary Canal*, Ed.: M. Dekker, NY, 15 pgs. of text.
Kleckner et al., (1977) J. Mol. Biol. 116:125–159.
Cardineau et al., (1987) J. Biol. Chem. 262(7):3344–3353.
Hooke et al., (1987) Infection and Immunity 55(1):99–103.
Levine et al., (1984) Infection and Immunity 43(2):515–522.
Maloy et al., (1981) J. of Bacteriology 145(2):1110–1112.
Marquez et al., (1985) Journal of Bacteriology 164(1):379–383.
Wiseman et al., (1984) Journal of Biol. Chem. 259(14):8907–8914.
Richaud et al., (1984) Journal of Biol. Chem. 259(23):14824–14828.
Bouvier et al., (1984) J. Biol. Chem. 259(23):14829–14834.
Obukowicz et al., (1986) Journal of Bacteriology 168(2):982–989.
Obukowicz et al., (1987) Gene 51:91–96.
Don et al., (1985) Journal of Bacteriology 161(1):85–90.
Don et al., (1985) Journal of Bacteriology 161(1):466–468.
Jagusztyn–Krynicka et al., (1982) Journal of General Microbiology 128:1135–1145.
Jacobs et al., (1986) PNAS 83:1926–1930.
Haziza et al., (1982) EMBO Journal 1:379–389.
Curtiss, (1986) Chem. Abst. 105(17):86, abstract No. 147242a.
Diderichsen, (1986) Chem. Abst. 105(21):201, abstract No. 185265t.
Cardineau, (1987) Chem. Abst. 107(19):157, abstract No. 169735g.
Curtiss et al., (1986) Chem. Abst. 105(11):121, abstract No. 92418e.
Curtiss, (1983) Chem. Abst. 99(18):381–382, abstract No. 146100y.
Curtiss et al., (1983) Chem. Abst. 99(21):182, abstract No. 170599e.
Ferrari et al., (1986) Chem. Abst. 104(9):106, abstract No. 63030w.

*Primary Examiner*—Nancy T. Vogel
*Attorney, Agent, or Firm*—Howell & Haferkamp, L.C.

[57] ABSTRACT

The invention encompasses methods of maintaining desired recombinant genes in a genetic population of cells expressing the recombinant gene. The methods utilize mutant cells which are characterized by a lack of a functioning native gene encoding an enzyme which is essential for cell survival, wherein this enzyme catalyzes a step in the biosynthesis of an essential cell wall structural component and the presence of a first recombinant gene encoding an enzyme which is a functional replacement for the native enzyme, wherein the first recombinant gene cannot replace the defective chromosomal gene. The first recombinant gene is structurally linked to a second recombinant gene encoding a desired product. Loss of the first recombinant gene causes the cells to lyse when the cells are in an environment where a product due to the expression of the first recombinant gene is absent. The invention also encompasses methods of creating and isolating mutant cells with the above characteristics. The cells of the invention are useful for commercial production of desired products, for components of vaccines for immunizing individuals, and for release into the environment.

16 Claims, 18 Drawing Sheets

```
                          -35
ATTCTGAAATGAGCTG TTGACA ATTAATCATCGGCTCG

-10
TATAAT GTGTGGAATTGTGAGCGGATAACAATTTCAC

SD                              Eco RI
AC AGGA AACAGACC ATG CCG GAA TTC GCA ATT
                 Met Pro Gln Phe Ala Ile

Sma I  Bam HI    Sal I      Pst I
CCC GGG GAT CCG TCG ACC TGC AGC CAA GCT CCC
Pro Gly Asp Pro Ser Thr Cys Ser Gln Ala Pro

Hind III     Sph I      Pst I
AAG CTT GCA TGC CTG CAG GTC
Lys Leu Ala Cys Leu Gln Val
```

Figure 6

SELECTIVE MAINTENANCE OF A RECOMBINANT GENE IN A POPULATION OF VACCINE CELLS

CROSS REFERENCE TO RELATED APPLICATION

This application is a continuation of application Ser. No. 07/990,361 filed Dec. 15, 1992, abandoned, which is a continuation of application Ser. No. 07/251,304 filed Oct. 3, 1988, abandoned which is a continuation-in-part of commonly owned application Ser. No. 07/106,072 filed Oct. 7, 1987, now abandoned.

REFERENCE TO GOVERNMENT GRANT

The United States Government has rights to this invention pursuant to Grant Nos. DE06669 and DE06673, awarded by the United States Public Health Service.

DESCRIPTION

1. Technical Field

The invention relates to materials and methodologies for preparing vaccines and recombinant DNA expression products, and more particularly to genetically-engineered microorganisms which are useful to express desired gene products because they are balanced lethals which can be maintained in a genetically stable population.

References Cited

Amann and Brosius (1985), Gene 40:193.
Bachmann in GENETIC MAPS 1987 (S. J. O'Brien ed., Cold Spring Harbor Laboratory) pp. 178–184.
Barrett, J. T., *Textbook of Immunology* 4th Ed., C. V. Mosby Co., St. Louis, MO (1983).
Buchanan et al (1987), Infect. Immun. 55:1000.
Buxton et al (1980), J. Gen. Microbiol. 120:283.
Cardineau and Curtiss (1987), J. Bio. Chem. 262:3344.
Curtiss et al (1965), J. Bacteriol. 89:28.
Curtiss et al (1982) in Microbial Drug Resistance (S. Mitsuhashi, ed.) vol. 3, pp 15–27.
Curtiss and Kelly (1987), Infect. Imm. 55:3035.
Davis, Dulbecco, Eisen, Ginsberg, and Wood, MICROBIOLOGY (Harper and Row).
Davis, Botstein, and Roth, ADVANCED BACTERIAL GENETICS (Cold Spring Harbor Laboratories).
Dean (1981), Gene 15:190.
DNA CLONING, Volumes I and II (D. N. Glover, ed., 1985).
Dul et al (1973), J. Bacteriol. 115:1212.
Guyer (1983), Meth. Enzymol. Vol. 101, 362.
Jagusztyn-Krynicka, et al (1982), J. Gen. Microbiol. 128:1135.
Kahn et al (1979), Meth. Enzymology 68:268.
Kleckner et al (1977), J. Mol. Biol. 116:125.
Lugtenberg et al (1973), J. Bacteriol. 113:96.
Maniatis, Fritsch and Sambrook, MOLECULAR CLONING: A LABORATORY MANUAL (Cold Spring Harbor Laboratories, 1982).
METHODS IN ENZYMOLOGY (Academic Press, Inc.);
Marquez et al (1985), J. Bacteriol. 164:379.
Miller, EXPERIMENTS IN MOLECULAR GENETICS (1972, Cold Spring Harbor Laboratory).
Miyaka et al (1972), J. Bacteriol. 112:950.
Nakayama et al (1988), Biotech. 6:693.
NUCLEIC ACID HYBRIDIZATION (B. D. Hames and S. J. Higgins, eds., 1984).
OLIGONUCLEOTIDE SYNTHESIS (M. J. Gait ed. 1984).
Perbal, A PRACTICAL GUIDE TO MOLECULAR CLONING (1984).
Sanderson and Roth in GENETIC MAPS 1987 (S. J. O'Brien, ed., Cold Spring Harbor Laboratory) pp. 155–177.
Schleifer and Kandler (1972), Bacteriol. Rev. 36:407.
Shepard et al (1980), Intl. J. Lepr. 48:371.
Umbarger (1978), Ann. Rev. Biochem. 47:533
VECTORS: A SURVEY OF MOLECULAR CLONING VECTORS AND THEIR USES (R. L. Rodriguez and D. T. Denhardt, eds., 1987, Butterworths);
Wijsman (1972a), Genet. Res. 20:269.
Wijsman (1972b), Genet. Res. 20:65.
U.S. Pat. No. 4,190,495.

2. Background Art

Genetically engineered microorganisms have widespread utility and importance. For example, they can be used to produce foreign proteins, and thus can be used industrially for synthesis of products such as interferons, insulin, growth hormone, etc.; they can also be used as vaccines to produce an immune response. In addition, they can be released into the environment to degrade environmental pollutants or even to kill insect pests afflicting agriculturally important crops. However, the genetically-engineered microorganism must often synthesize a gene product from which it derives no benefit, and the high level expression of the recombinant protein may be deleterious to the microorganism. Thus, the genetically engineered microorganism may be at a selective disadvantage relative to the same type of microorganism which doesn't produce the cloned gene product. As a result, spontaneous segregants which have lost the DNA sequence specifying the desired gene product quickly outpopulate the genetically-engineered microorganism. This occurs whether the microorganisms grow in a fermenter, in the soil, on a plant, or in an animal.

One method for applying selective pressure to a bacterial population is to insert the recombinant gene encoding the desired polypeptide in a plasmid which also contains a gene encoding antibiotic resistance. Most cloning vectors currently in use have one or more genes specifying resistance to antibiotics. Thus, antibiotics can be added to the culture medium for growth of genetically-engineered microorganisms to kill those bacteria which have lost the recombinant plasmid. This practice has several drawbacks. First, it is expensive to add antibiotics to growth medium. Second, since antibiotic resistance is often based upon the synthesis of drug inactivating enzymes, cells remain phenotypically drug resistant for a number of cell generations after the loss of genes for drug resistance, which are associated with genes specifying the desired recombinant DNA product. Third, unless the cloned antibiotic resistance gene is contiguous with the gene expressing the desired product, the latter DNA sequence can be deleted by illegitimate recombination without loss of antibiotic resistance. The result is a bacterium that is resistant to antibiotics, but which lacks the ability to synthesize the desired product. Fourth, in the case of genetically-engineered bacteria to be used as a live vaccine, the Food and Drug Administration has refrained from approving strains which express antibiotic resistance.

An alternative to antibiotic resistance for maintaining a recombinant plasmid and/or a cloned gene in a genetically-engineered microorganism is using a mutant bacterium that lacks a critical biosynthetic enzymer and supplying the wild-type gene for that enzyme on the plasmid cloning vector. Kahn et al (1979) and Dean (1981). Unfortunately, this is impractical in many situations. The use of mutants which are missing enzymes involved in the biosynthesis of amino acids, purines, pyrimidines, and vitamins often does not preclude the growth of these mutants since the end-product of the pathway which is required for growth is often furnished by the environment. For example, inexpensive media used for the growth of recombinant organisms in fermenters often contain these end-products. In addition, particularly in the case of live vaccines, the end-product may be supplied in vivo by the vaccinated host.

It has been suggested that the problems of genetic instability of genetically-engineered microorganisms possessing a cloned gene on a plasmid can be alleviated by integrating the cloned gene into the chromosome of the microorganisms. This suggestion has at least one flaw. If a foreign cloned gene sequence on a plasmid can be lost by illegitimate recombination, the same type of recombination could also occur when the cloned gene is integrated into the bacterial chromosome. That is, the structural and enzymatic events resulting in the deletion of DNA sequences by illegitimate recombination are basically similar whether the DNA sequence resides on a plasmid or is an integral part of the bacterial chromosome. Moreover, integration of the recombinant gene into the chromosome overcomes many of the potential benefits of having it reside on the plasmid. For example, control of plasmid copy number of the plasmid containing the cloned gene provides a mechanism for increasing the product yield. It also offers a mechanism for temporally controlling the expression of the product so that high level expression occurs at less deleterious times during the growth cycle.

All bacteria have a peptidoglycan layer of the cell wall which imparts shape and rigidity. The peptidoglycan is made of a polymer of repeating muramic acid-N-acetylglucosamine and is cross-linked by short peptides. In all Gram-negative bacteria and in Mycobacterium and in Nocardia species of Eubacteria, the peptide is composed of L-alanine, D-glutamic acid, mesodiaminopimelic acid (DAP), and D-alanine. In most Gram-positive microorganisms the DAP is replaced by its decarboxylation product L-lysine.

DAP is synthesized in six enzymatic steps from beta-aspartate semialdehyde, which, in turn, is synthesized in two steps from L-aspartic acid. In the first step, L-aspartic acid is phosphorylated by one of several (usually three) beta-aspartokinases which are encoded by several (usually three) separate genes regulated independently by repression and/or feedback inhibition of the gene products by the ultimate end products L-threonine, L-methionine, and L-lysine. Beta-aspartophosphate is converted in one step to beta-aspartic semialdehyde by beta-aspartic semialdehyde dehydrogenase, the product of the asd gene. Mutants with a point mutation in or deletion of the asd gene as well as mutants with mutations in any of the six genes specifying the enzymes for converting beta-semialdehyde to DAP have an obligatory requirement for DAP in all media. When DAP-requiring mutants are deprived of DAP they undergo DAP-less death, and lyse, releasing their contents.

The inclusion of asd, and thus dap, mutations in strains of bacteria affords biological containment, since such mutant strains are unable to survive in environments other than a carefully controlled laboratory environment. The basis for this has been extensively described in U.S. Pat. No. 4,190, 495.

The gene for aspartic beta-semialdehyde dehydrogenase from *Streptococcus mutans* PS14 (UAB62) has been cloned and expressed in asd mutants of *E. coli*. Jagusztyn-Krynicka, et al (1982); Curtiss et al (1982). Subsequently, the *S. mutans* asd gene has been sequenced. Cardineau and Curtiss (1987).

In gram positive microorganisms as well as in gram-negative bacteria, the peptide cross-linking repeating muramic acid-N-acetylglucosamine polymers contain D-alanine. D-alanine is synthesized from L-alanine by alanine racemase, the product of the alr gene (*E. coli*) or the dal gene (*B. subtilis*) and then is converted to a D-alanyl-D-alanine dipeptide by the enzyme D-alanyl-D-alanine ligase, the product of the ddl gene. Following addition to the L-alanyl D-glutamyl DAP or L-alanyl-D-glutamyl-L lysine tripeptide which is attached to one muramic acid-N-acetylglucosamine polymer to form a pentapeptide, the terminal D-alanine is cleaved during the enzymatic cross-linking reaction to the next muramic acid-N-acetylglucosamine polymer. Mutants of either *E. coli* or *Bacillus subtilis* lacking the ability to synthesize D-alanine or to synthesize D-alanyl-D-alanine lyse in media devoid of D-alanine or of the dipeptide. alr *E. coli* mutants lacking alanine racemase have been isolated [Wijsman (1972a)] as have dal mutants of *B. subtilis* also lacking alanine racemase [Dul et al (1973)]. ddl mutants lacking D-alanyl D-alanine ligase have been isolated in *E. coli* [Wijsman (1972b), Miyakawa et al (1972), Lugtenberg et al (1973)] and *B. subtilis*. As in the case of the asd and dap mutations, the inclusion of alr (or dal) and/or ddl mutations in strains of bacteria affords biological containment, since such mutant strains are unable to survive in environments other than a carefully controlled laboratory environment.

DISCLOSURE OF THE INVENTION

The various embodiments of the invention feature genetically engineered host cells which are useful for the expression of desired gene products because they are balanced lethals which can be maintained in a genetically stable population.

Accordingly, one aspect of the invention is a method of maintaining a desired recombinant gene in a genetic population of cells expressing said recombinant gene, comprising growing genetically engineered cells characterized by:

a) a lack of a functioning native chromosomal gene encoding an enzyme 1, which is essential for cell survival, wherein the enzyme 1 catalyzes a step in the biosynthesis of an essential cell wall structural component;

b) the presence of a first recombinant gene encoding an enzyme 2 which is a functional replacement for enzyme 1, wherein said first recombinant gene cannot replace the defective chromosomal gene;

c) the presence of a second recombinant gene encoding a desired polypeptide;

d) physical linkage between the first recombinant gene and the second recombinant gene, wherein loss of the first recombinant gene causes the cells to lyse when the cells are in an environment where a product due to the expression of the first recombinant gene is absent;

and wherein the growing is in an environment in which the lack of the first recombinant gene causes the cells to lyse.

Another aspect of the invention are the above described genetically engineered cells.

Still another aspect of the invention is a method of creating and isolating bacteria with a mutation in a gene encoding an enzyme which catalyzes a step in the biosynthesis of an essential cell wall structural component, wherein the cell wall component is synthesized from DAP, comprising:

a) growing and mutagenizing parental bacteria in DAP containing media; and b) selecting for mutant bacteria using growth medium which allows expression of auxotrophy but that contains DAP and an antibiotic which interferes with cell wall biosynthesis in said bacteria.

Yet another aspect of the invention is a method of creating and isolating bacteria containing a mutation in a gene encoding beta-aspartate semialdehyde dehydrogenase (asd), comprising:

a) introducing a deletion into a chromosomal gene of a bacterium using a transposon to cause the deletion; and b) isolating mutants containing deletions in the gene encoding asd, wherein the isolating medium contains DAP.

Still another aspect of the invention is a recombinant bacterial strain containing a deletion mutation in a gene encoding asd, which is useful for the construction of Asd⁻ mutants, said strain being selected from the group consisting of *E. coli* K-12 Chi2108 and *S. typhimurium* Chi3520, and mutants thereof.

Another aspect of the invention is a recombinant plasmid, useful for complementing a bacterial strain with an Asd⁻ phenotype, containing a first recombinant gene encoding asd, and containing restriction enzyme sites wherein a second recombinant gene encoding a desired product may be inserted.

Yet another aspect of the invention is a vaccine comprising an attenuated strain of bacteria characterized by:

a) a lack of a functioning native chromosomal gene encoding an enzyme 1, which is essential for cell survival, wherein the enzyme 1 catalyzes a step in the biosynthesis of an essential cell wall structural component;

b) the presence of a first recombinant gene encoding an enzyme 2 which is a functional replacement for enzyme 1, wherein said first recombinant gene cannot replace the defective chromosomal gene;

c) the presence of a second recombinant gene encoding a desired polypeptide;

d) physical linkage between the first recombinant gene and the second recombinant gene, wherein loss of the first recombinant gene causes the cells to lyse when the cells are in an environment where a product due to the expression of the first recombinant gene is absent; and wherein the cells are in a pharmaceutically acceptable excipient, wherein the bacteria are present at a pharmacologically effective dose.

Yet another aspect of the invention is a plasmid selected from the group consisting of pYA248, plasmids derived therefrom by insertion of a gene encoding a polypeptide in a restriction enzyme site, and mutants thereof.

Still another aspect of the invention is a plasmid selected from the group consisting of pYA292, plasmids derived therefrom by insertion of a gene encoding a polypeptide in a restriction enzyme site, and mutants thereof.

Another aspect of the invention is a bacterial strain selected from the group consisting of Chi6097 containing PYA 232, Chi2978, Chi3520, Chi4072 containing PYA 248, Chi3008, Chi2108, and Chi6097 containing pYA292.

BRIEF DESCRIPTION OF THE DRAWINGS

FIG. 6 shows the nucleotide sequence of the Ptrc promoter and multiple cloning site in pYA 248.

MODES FOR CARRYING OUT THE INVENTION

A. Definitions

Figure 1:
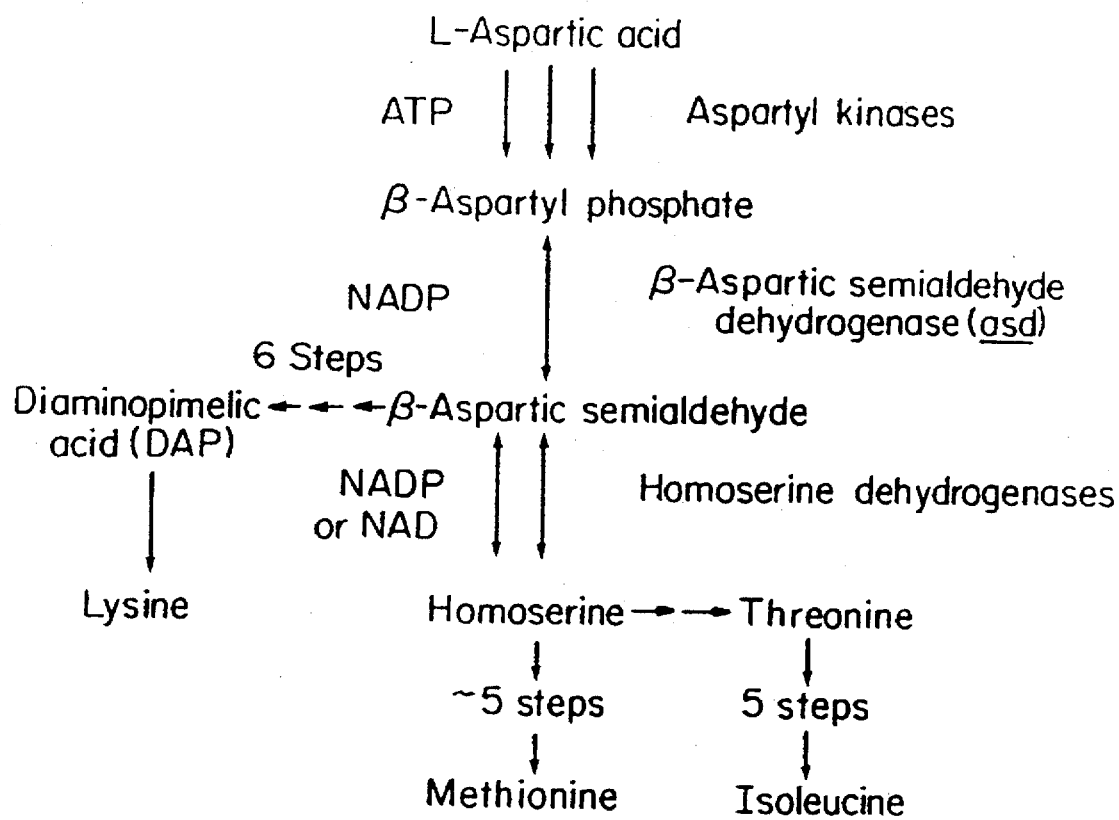
FIG. 1 is d flow chart for the biosynthesis of the aspartate family of amino acids.

"Recombinant host cells", "host cells", "cells" and other such terms denoting microorganisms are used interchangeably, and refer to cells which can be, or have been, used as recipients for recombinant vectors or other transferred DNA, and include the progeny of the original cell transfected. It is understood that the progeny of a single parental cell may not necessarily be completely identical in genomic or total DNA complement as the original parent, due to accidental or deliberate mutation. Progeny of the parental cell which are sufficiently similar to the parent to be characterized by the relevant property, for example, the substitution of a native gene encoding an essential enzyme with a cloned gene linked to a structural gene encoding a desired gene product.

"Control sequence" refers to DNA sequences which are necessary to effect the expression of coding sequences to which they are ligated. Generally such control sequences include promoter and ribosome binding site. The term "control sequences" is intended to include, at a minimum, all components whose presence is necessary for expression, and may also include additional components whose presence is advantageous, for example, operators.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

"Gram negative bacteria" include cocci, nonenteric rods, and enteric rods. The genera of gram negative bacteria include, for example, Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agribacterium, Azotobacter, Spirilla, Serratia, Vibrio, Rhizobium, Chlamydia, Rickettsia, Trepanema, and Fusobacterium, "Gram positive bacteria" include cocci, nonsporulating rods, and sporulating rods. The genera of gram positive bacteria include, for example, Actinomyces, Bacillus, Clostridium, Corynebacterium, Erysipelothrix, Lactobacillus, Listeria, Mycobacterium, Myxococcus, Nocardia, Staphylococcus, Streptococcus, and Streptomyces.

"Mycobacteria" are defined on the basis of their distinctive staining property, i.e., they resist decolorization with acidified organic solvents, and on the presence of long chain (approximately 60 carbons) mycolic acids.

A "native chromosomal gene" is one which occurs in the chromosome of a wild-type organism, for example, the gene encoding aspartic semi-aldehyde dehydrogenase (asd) in *E. coli* or *Salmonella*, the genes encoding alanine racemase, and the genes encoding D-alanyl-D-alanine ligase. Other examples of native genes are described infra.

A "recombinant gene", as used herein, is defined as an identifiable segment of polynucleotide within a larger polynucleotide molecule that is not found in association with the larger molecule in nature.

An "essential cell wall component" is one which is necessary to maintain the structural integrity of the cell wall, without which the cell is osmotically sensitive. Osmotic sensitivity of a strain can be measured by placing the cells in hypotonic media, and measuring the salt concentration at which the cell lyses, for example, by a change in the turbidity of the cell suspension; the osmotic sensitivity of the mutant strain is compared to that of a wild-type strain which contains the essential cell wall component. A characteristic of osmotically sensitive cells which result from a lack of the essential cell wall component is that increased cellular protein mass, for example resulting from protein synthesis, causes the cells to lyse. Examples of essential cell wall components include glycans, particularly peptidoglycans in prokaryotes, chitin in fungal cell walls, and cellulose in plant cell walls.

A "peptidoglycan" is a typical constituent of cell walls of almost all procaryotic cells, which is responsible for the rigidity of the cell wall. Peptidoglycans are a family of macromolecules containing acylated amino sugars and three to six different amino acids; the heteropolymers contain glycan strands crosslinked through short peptides. Peptidoglycans have been reviewed in Schleifer and Kandler (1972).

As used herein, "DAP" refers to both stereoisomers of diaminopimelic acid and its salts, i.e., both the LL- and meso- forms, unless otherwise shown by specific notation.

The gene symbols for mutant strains utilized herein are those described by Bachmann (1987), and Sanderson and Roth (1987). The symbols used for transposons, particularly Tn10, follow the convention described in Bukhari et al (1977).

An "individual" treated with a vaccine of the invention is defined herein as including all vertebrates, for example, mammals, including domestic animals and humans, various species of birds, including domestic birds, particularly those of agricultural importance. In addition, mollusks and certain other invertebrates have a primitive immune system, and are included as an "individual".

"Transformation", as used herein, refers to the insertion of an exogenous polynucleotide into a host cell, irrespective of the method used for the insertion, for example, direct uptake, transduction, or conjugation. The exogenous polynucleotide may be maintained as a plasmid, or alternatively, may be integrated within the host genome.

B. General Description

The practice of the present invention will employ, unless otherwise indicated, conventional techniques of cell culture, molecular biology, microbiology, recombinant DNA, and immunology, which are within the skill of the art. Such techniques are explained fully in the literature. See, e.g., Maniatis, Fritsch and Sambrook, MOLECULAR CLONING: A LABORATORY MANUAL (1982); DNA CLONING, Volumes I and II (D. N. Glover, ed., 1985); OLIGONUCLEOTIDE SYNTHESIS (M. J. Gait ed., 1984); NUCLEIC ACID HYBRIDIZATION (B. D. Hames and S. J. Higgins, eds., 1984); B. Perbal, A PRACTICAL GUIDE TO MOLECULAR CLONING (1984); the series, METHODS IN ENZYMOLOGY (Academic Press, Inc.); VECTORS: A SURVEY OF MOLECULAR CLONING VECTORS AND THEIR USES (R. L. Rodriguez and D. T. Denhardt, eds., 1987, Butterworths); and J. H. Miller, EXPERIMENTS IN MOLECULAR GENETICS (1972, Cold Spring Harbor Laboratory).

All patents, patent applications, and publications mentioned herein, whether supra or infra, are hereby incorporated by reference.

The invention focuses, in part, on genetically engineered host cells which can be maintained as a genetically stable population, wherein the host cells express a desired recombinant gene product. The host cells in this population characteristically have had inactivated a native gene encoding an enzyme which is essential for cell survival in that the enzyme catalyzes a step in the biosynthesis of an essential cell wall component. In addition, the function of the native gene is replaced by a recombinant gene, which cannot replace the defective chromosomal gene, whose expression is operably linked to the expression of the desired gene product. The invention describes methods for creating and isolating cells which are suitable host cells. Plasmids which are suitable for transforming the host cells, which contain the replacement recombinant enzyme and into which the gene encoding the desired polypeptide may be inserted are also described. The cells of the invention are suitable for use for the production of desired polypeptides in industrial settings, for example, by growth in fermenters. These cells may also be components of vaccines, particularly live vaccines.

One characteristic of the host cells of the invention is that their cell walls contain a structural polymer, for example, peptidoglycan, or chitin, or cellulose, which is necessary to maintain the structural integrity of the cell, i.e., without which the cell becomes osmotically sensitive. Thus, the host cells may be prokaryotic cells, such as, for example, bacteria which contain peptidoglycan, or eukaryotic cells, such as, for example, fungi which contain chitin, or plant cells which contain cellulose. Preferably, the host cells of the invention are prokaryotic cells which contain peptidoglycan as part of the cell wall. The peptidoglycan may be one which, for example, contains D-alanine in the cross-linking peptide. Host cells with this type of cross-linking are known in the art. Most preferably, the host cells of the invention are prokaryotic cells in which the peptidoglycan is comprised of DAP. Examples of host cells in which the peptidoglycan is comprised of DAP are known to those of skill in the art, for example, see Schleifer and Kandler (1972), and include, for example probably all gram negative bacteria, as well as numerous other organisms, such as some species of bacilli, clostridia, lactobacilli, corynebacteria, prioioni-bacteria, Actinomycetales, Myxobacteriales, Rickettsiae, and blue-green algae. A review of the methods by which a peptidoglycan may be characterized as containing DAP is presented in Schleifer and Kandler (1972).

Another characteristic of the host cells of the invention is that they have been mutated, so that a native chromosomal gene encoding an enzyme which catalyzes a step in the biosynthesis of the essential cell wall component, is not functional, i.e., does not yield a functional enzyme. Methods for mutating cells to create the host cells of the invention are known in the art, and include, for example, chemical mutagenesis, UV mutagenesis, and mutations induced via the action of transposons. See, e.g., Miller (1972); Davis, Botstein and Roth; and Methods in Enzymology. Although host cells carrying point mutations in the above described genes are included in the invention, it is preferable to use host cells carrying deletion mutations in these genes, since deletion mutants do not generally revert.

Enzymes which catalyze the biosynthesis of the cell wall component and its precursors are known in the art. For example, in the synthesis of peptidoglycans, the enzyme may be one which catalyzes the insertion of the cross-linking peptide, for example, D-alanyl-D-alanine ligase, or of the synthesis of the carbohydrate polymer, or it may be an enzyme which catalyzes a step in the biosynthesis of a precursor, for example, DAP. FIG. 1 shows the pathway for the biosynthesis of the aspartate family of amino acids, of which both stereoisomers of DAP are members. For a review of the biosynthesis of this family of amino acids, see Umbarger (1978). Examples of genes encoding enzymes which catalyze steps in the biosynthesis of DAP are known in the art for a variety of organisms, see, for example, GENETIC MAPS 1987 (S. J. O'Brien, ed., Cold Spring Harbor Laboratories), and include, for example, in *S. typhimurium* the dapA and dapB genes and for example, in *E. coli*, the dapA, dapB, dapC, dapD, and dapE genes. Another enzyme which exemplifies one of this type, i.e., is essential for DAP synthesis, is aspartate semi-aldehyde dehydrogenase (ASD), which is encoded in the asd gene.

Described in the Examples, infra, are methods for introducing deletion mutations in the asd gene (delta-asd) in a diversity of bacterial strains that are members of the Enterobacteriacae, and a method to isolate asd mutants of other Gram-negative bacteria and mycobacteria. Table 1 lists the *E. coli* K-12 and *S. typhimurium* LT-2 strains used to isolate asd mutants and their derivatives; the Asd⁻ strains listed therein are examples of strains which can be used to construct other strains, utilizing transposon techniques, as described infra. Asd⁻ strains are also described in U.S. Pat. No. 4,190,495.

TABLE 1

Bacterial strains

| Strain number | Parent strain/ plasmid | Relevant genotype | Derivation |
|---|---|---|---|
| A. *Escherichia coli* strains | | | |
| X289 | K-12/F⁻ | prototroph glnV42 | Curtiss collection |
| X2108 | K-12/F⁻ | leu-50 tsx-98 proB59 Δ69[lacZOPI] Δ40[gal-uvrB] rpsL206 ΔasdA4 argH70 | HNO₂-induced Asd⁻ mutant of X2087 |
| X2230 | K-12/F⁻ | thr-1 leu-6 proA2 his-4 metB1 lacY1 galK2 ara-14 tsx-33 thi-1 thyA12 deoB6 supE44 dam-3 (mtl-1) | dam-3 derivative of X2234 (M. G. Marinus) |
| LE392 | K-12/F⁻ | lacY1 glnV44 λ⁻ galK2 galT22 tyrT58 metB1 hsdR514 trpR55 | P. Leder |
| X2637 | K-12/F⁻ | tsx-63 purB41 glnV42 λ⁻ pyrF30 his-53 tte-1 ΔasdA4 xyl-14 cycB2 cycA1 | Plcml(X2108 → X660 with sel'n for AroB⁺ Asd⁻ |
| X2842 | K-12/F⁻ | prototroph, suppressor-free | Curtiss collection |
| X2978 | K-12/F⁻ | tax-63 purE41 glnv42 λ⁻ pyrF30 his-53 tte-1 zhf-2::Tn10 xyl-14 cycB2 cycA1 | P1L4(X2842::Tn10 library) → X2637 with sel'n for Tc^r Asd⁺ |
| X2979 | K-12/F⁻ | tsx-63 purE41 glnv42 λ⁻ pyrF30 his-53 tte-1 ΔasdA4 zhf-2::Tn10 xyl-14 cycB2 cycA1 | P1L4(X2978 → X2637 with sel'n for Tc^r |
| X2981 | K-12/F⁻ | Δ41[proB-lacYZ] glnV42 λ⁻ tte-1 ΔasdA4 zhf-2::Tn10 cycA1 | P1L4(X2979) → X354 with sel'n for Tc^r Asd⁻ |
| X2984 | K-12/F⁻ | Δ41[proB-lacYZ] λ⁻ tte-1 ΔasdA4 Δ[zhf-2::Tn10] cycA1 | FA^s Tc^s derivative of X2981 |
| CC118 | K-12/F⁻ | araD139 Δ(ara, leu)7697 ΔlacX74 phoAΔ20 galE galR recA1 rpsE argE_am rpoB thi | Manoil and Beckwith^a |
| X6094 | K-12/F⁻ | lacY1 glnV44 λ⁻ galK2 galV22 tyrT58 ΔasdA4 zhf-2::Tn10 metB1 hsdR514 trpR55 | P1L4(X2981) → X2602 with sel'n for Tc^r Asd⁻ |
| JM83 | K-12/F⁻ | ara Δ[lac-pro] rpsL thi φ80dlacZ ΔM15 | Viera and Messing^b |
| X6096 | K-12/F⁻ | ara Δ[lac-pro] rpsL ΔasdA4 zhf-2::Tn10 thi φ80dlacZ ΔM15 | P1L4(X2981) → JM83 with sel'n for Tc^r Asd⁻ |
| X6097 | K-12/F⁻ | ara Δ[lac-pro] rpsL ΔasdA4 Δ[zhf-2::Tn10] thi φ80dlacZ ΔM15 | Fa^s Tc^s derivative of X6096 |
| Y1090 | K-12/F⁻ | ΔaraD139 ΔlacU169 Δlon tyrT trpC22::Tn10 rpsL hsdR (pBR322 lacI^q) | Promega Biotech |
| B. *Salmonella typhimurium* strains | | | |
| X3000 | LT2-Z/pStLT100 | prototroph, suppressor-free | Curtiss collection |
| X3008 | LT2-Z/pStLT100 | asdA15 | HNO₂-induced Asd⁻ mutant of X3000 |
| X3013 | LT2-Z/pStLT100 | zhf-1::Tn10 | from P22(X3000::Tn10 library) → X3008 with sel'n for Tc^r Asd⁺ |

TABLE 1-continued

Bacterial strains

| Strain number | Parent strain/ plasmid | Relevant genotype | Derivation |
|---|---|---|---|
| X3021 | LT2-Z/pStLT100 | Δ[zhf-1::Tn10] ΔasdA1 P22ª | FA$^r$ Tc$^s$ derivative of X3013 |
| X3105 | SR-11/pStSR100 | zhf-1::Tn10 P22$^i$ | P22(X3013) → X3041 with sel'n for Tc$^r$ |
| X3115 | SR-11/pStSR100 | ΔasdA3 P22$^i$ | ATCC 39961 (FA$^r$ sel'n of X3105) |
| SGSC452 | LT2-Z/pStLT100 | leu hsdLT galEtrpD2 rpsL120 metE551 metA22 hsdSA hsdSB ilv | Bullas and Ryu$^c$ |
| DB4673= TS736 | LT2-Z/pStLT100 | galE496 trpB2 flaA66 rpsL120 xyl-404 val metE551 metA22 ΔmalB hsdSA29 hsdL6/F'112 (malE malF malK lamB from E. coli) | Palva and Liljestrom$^d$ |
| X3385 | LT2-Z | hsdL6 galE596 trpB2 flaA66 his-6165 rpsL120 xyl-404 metE551 metA22 lamB$^+$ (E. coli) Δzja:Tn10 hsdSA29 val | cured derivative of AS68 (E. T. Palva) |
| X3457 | LT2-Z/pStLT100 | nadA540::Tn10 Δ[galE-uvrB]-1005 | P22HTint(SL5400) → X3000; lysate from Bruce Stocker. |
| X3477 | LT2-Z | hsdL6 Δ[galE-uvrB]-1005 flaA66 rpsL120 xyl-404 lamB$^+$ (E. coli) Δ[zja::Tn10] hsdSA29 | P22HTint(SL5400) → X3385 with subsequent sel'n against auxotrophic markers (val, metE, metA) using P22HTint(X3000) |
| DB9031 | LT2-Z/pStLT100 | zeh-4::Tn10 | Tn10 95% linked to gyrA |
| X3520 | LT2-Z/pStLT100 | ΔasdA1 zhf-4::Tn10 | P22HTint(X3536) → X3021 with sel'n for Tc$^r$ (Asd$^-$); P22HTint(X3021 Tc$^r$ Asd$^-$)$^e$ → X3000 with sel'n for Tc$^r$ (Asd$^-$) |
| X3536 | LT2-Z/pStLT100 | zhf-4::Tn10 | from P22HTint(X3324::Tn10 library) → X3000; P22HTint(X3000::Tn10 library) → X3021 with sel'n for Tc$^r$ Asd$^+$; P22HTint(X3021 Tc$^r$)$^e$ → X3000 with sel'n for Tc$^r$ |
| X3537 | LT2-Z/pStLT100 | zhf-3::Tn10 | from P22HTint(X3324::Tn10 library) → X3000; P22HTint(X3000::Tn10 library) → X3021 Tc$^r$)$^e$ → X3000 with sel'n for Tc$^r$ |
| X3538 | LT2-Z/pStLT100 | zhf-3::Tn10 | P22HTint(X3537) → X3021 with sel'n for Tc$^r$ (Asd$^-$); P22HTint(X3021 Tc$^r$ Asd$^-$)$^e$ → X3000 with sel'n for Tc$^r$ (Asd$^-$) |
| X3628 | LT2-Z/pStLT100 | Δ[zhf:3::Tn10] ΔasdA13 | FA$^r$ Tc$^s$ Asd$^-$ derivative of X3537 |
| X3629 | LT2-Z | hsdL6 Δ[galE-uvrB]-1005 flaA66 rpsL120 zhf-3::Tn10 xyl-404 lamB$^+$ (E. coli) Δ[zja::Tn10] hsdSA29 | P22HTint(X3537) → X3477 with sel'n for Tc$^r$ Asd$^+$ |
| X3630 | LT2-Z | hsdL6 Δ[galE-uvrB]-1005 flaA66 rpsL120 ΔasdA13 xyl-404 lamB$^+$ (E. coli) Δ[zja::Tn10] hsdSA29 | P22HTint(X3628) → X3629 with sel'n for FA$^r$ Asd$^+$ |
| X3638 | LT2-Z | hsdL6 Δ[galE-uvrB]-1005 flaA66 rpsL120 zhf-4::Tn10 xyl-404 lamB$^+$ (E. coli) Δ[zja::Tn10] hsdSA29 | P22HTint(X3536) → X3477 with sel'n for Tc$^r$ Asd$^+$ |
| X3647 | LT2-Z/pStLT100 | Δ[zhf-4::Tn10] ΔasdA14 | Fa$^r$ Tc$^s$ Asd$^-$ derivative of X3536 |
| X3656 | LT2-Z/pStLT100 | leu hsdLT galE trpD2 rpsL120 ΔasdA1 zhf-4::Tn10 metE551 metA22 hsdSA hsdSB ilv | P22HTint(X3520) → X3179 with sel'n for Tc$^r$ Asd$^-$ |
| X4064 | SR-11/pStSR100 | gyrA1816 Δcya-1 Δcrp-1 | FA$^r$ Tc$^s$ derivative of X4055 (Curtiss and Kelly, submitted) |
| X4070 | SR-11/pStSR100 | gyrA1816 Δcya-1 Δcrp-1 ΔasdA1 zhf-4::Tn10 | P22HTint(X3520) → X4064 with sel'n for Tc$^r$ Asd$^-$ |
| X4072 | SR-11/pStSR100 | gyrA1816 Δcya-1 Δcrp-1 ΔasdA1 Δ[zhf-4::Tn10] | FA$^r$ Tc$^s$ derivative of X4070 |

$^a$(1985) Proc. Natl. Acad. Sci. USA 82:8129.
$^b$(1982) Gene 19:259–268.
$^c$(1983) J. Bact. 156:471–474
$^d$(1981) Mol. Gen. Genet. 181:153–157
$^e$Since X3021 is lysogenic for P22, P22HTint was propagated on the X3021 transductant following UV-induction (15 sec. at 5 J/m$^2$) of the prophage. The resulting lysate was used to transduce X3000.

Standard mutagenesis and mutant enrichment protocols are not efficient for the recovery of asd mutants, since a mutant with a requirement for DAP undergoes lysis and death in the absence of DAP. Thus, previously isolated asd mutants were discovered indirectly and by chance, or by brute-force screening of millions of potential mutants. The invention encompasses an efficient procedure for the selective enrichment and isolation of asd mutants.

In a synthetic medium, asd mutants require L-methionine, L-threonine, and DAP for growth. The requirement for L-methionine and L-threonine is satisfied by homoserine, which is a common precursor to both methionine and threonine (see FIG. 1). Mutagenesis of an *E. coli* or *S. typhimurium* strain followed by an ampicillin-cycloserine procedure for the enrichment of auxotrophic mutants seldom, if ever, recovers mutants with a sole requirement for homoserine. Curtiss et al (1965) describe a cycloserine-enrichment procedure for selecting auxotrophs, and a modification of that procedure also employing ampicillin is included herein, in the Examples. The reason that homoserine-requiring auxotrophs are seldom isolated is that beta-aspartic semialdehyde is converted to homoserine by either of two dehydrogenases which are encoded in two genes. The probability of inactivating both genes in a single cell is exceedingly small, and thus the homoserine-requiring auxotrophs may not be detected by random screening techniques.

This problem is overcome by the discovery that the inclusion of DAP in all media during mutagenesis, and enrichment or selection using the ampicillin-cycloserine technique, leads to the recovery of asd mutants that require both homoserine and DAP. Ampicillin and cycloserine both inhibit cell wall synthesis in growing cells capable of protein synthesis, but are without effect on auxotrophic mutants unable to synthesize proteins because of the absence of nutritional requirements. The asd mutant strains Chi3008 and Chi2108 (see Table 1), which are *S. typhimurium* and *E. coli* strains, respectively, were isolated using this procedure. The Asd⁻ phenotype of Chi3008 is due to a point mutation in the asd gene, and thus the frequency of reversion to Asd⁺ is fairly high. On the other hand, the Asd⁻ phenotype of Chi2108 results from a deletion in the asd gene, thus, the reversion frequency is very low.

Strains carrying mutations of the asd gene, particularly desirable deletion mutations, can be generated by techniques utilizing transposons. Transposons can be added to a bacterial chromosome at many points. The characteristics of transposon insertion and deletion have been reviewed in Kleckner (1977). For example, the transposon Tn10, which confers resistance to tetracycline (and sensitivity to fusaric acid) can be used to create delta-asd mutants in a variety of bacterial species, including, for example, *E. coli* and *S. typhimurium*.

One method to create delta-asd mutants in *E. coli* and *S. typhimurium*, is described in the Examples, infra. First, a library of random Tn10 insertions in the chromosomes of the bacteria is created utilizing an appropriate transposon vector, for example, lambda-NK561 for *E. coli* (Kleckner et al (1977)) with a lambda-sensitive strain of *S. typhimurium*, an example of which is Chi3324 (Table 1). A suitable transducing phage, for example, P1L4 or P22HT int, for *E. coli* and *S. typhimurium*, respectively, which has been propagated on the Tn10 library in the appropriate species, is used to transduce Asd⁻ mutants of that species, and bacteria containing an Asd⁺ Tc$^r$ phenotype are selected. Examples of asd⁻ strains which can be used are the *E. coli* strain Chi2108, and the *S. typhimurium* strain Chi3008 (see Table 1). Since single events are more probable than double events, most transductants, for example Chi2978 and Chi3013 (see Table 1) will have Tn10 closely linked to the asd gene. Selection for fusaric acid resistance, which results from deletion of Tn10 and adjacent DNA sequences, yields delta-asd mutants in which all or portions of the closely linked asd gene have been deleted. The delta-asdA1 mutation in the *S. typhimurium* Chi3021 strain was isolated from Chi3013 (Table 1) using this procedure.

Figure 14:
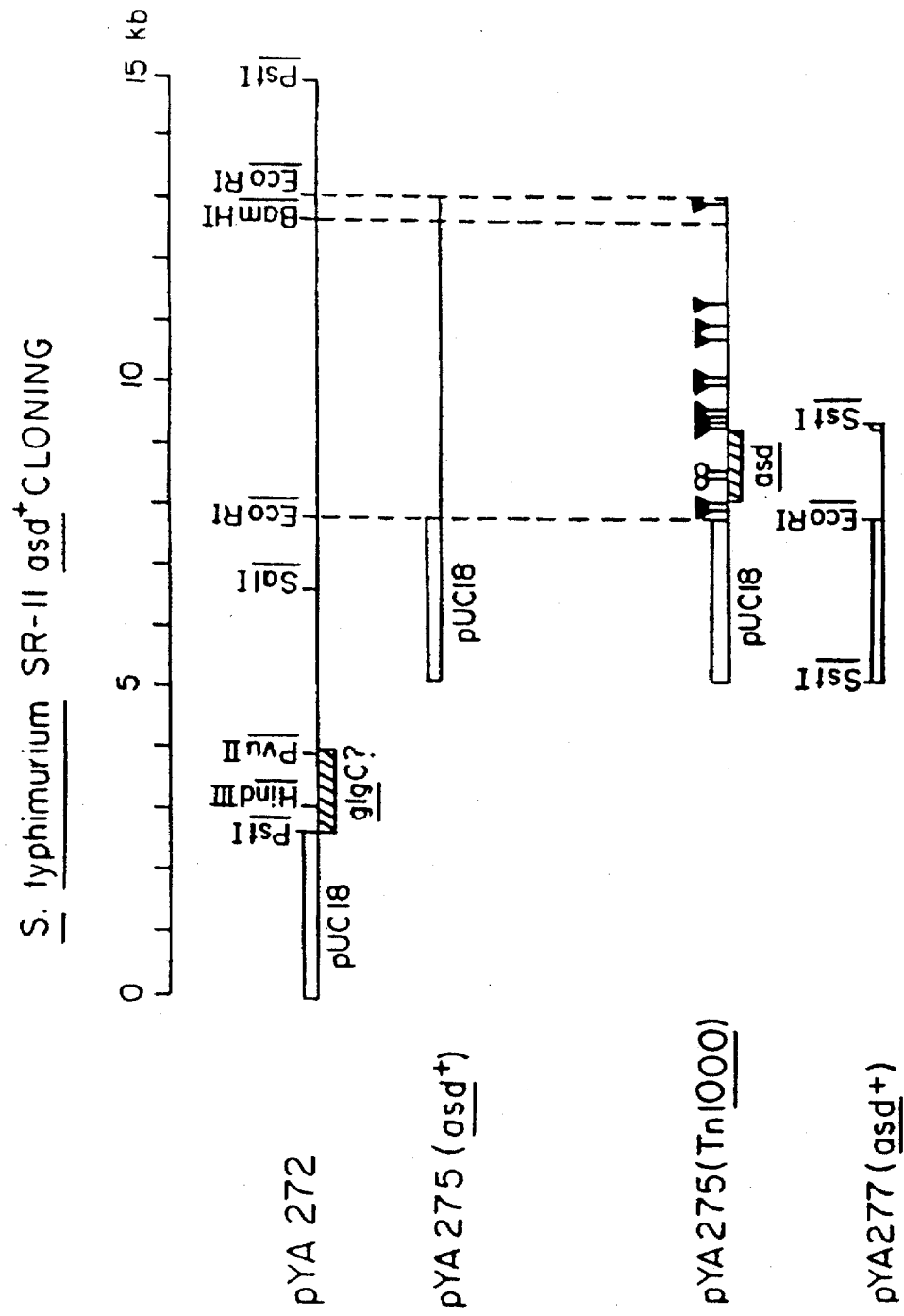
FIG. 14 is a chart showing the construction and properties of pYA272, pYA275 (with and without Tn1000 insertions) and pYA277.

Deletion mutations can also be introduced into the bacterial chromosome by using recombinant DNA techniques. Thus the asd gene of *S. typhimurium* has been cloned in pUC18 to yield pYA272 following subcloning in transposon mutagenesis to delimit the extent of the *S. typhimurium* asd gene in pYA275 (FIG. 14). Based on this information the asd gene can be deleted from pYA272, and the derived plasmid introduced into an asd⁺ *S. typhimurium* strain to allow for homologous recombination leading to cells that have the genetically engineered delta-asd mutation in the choromosome as well as in the plasmid. The culture is then grown at elevated temperatures, for example, 43° C., in the presence of low concentrations of novobiocin, plated on medium devoid of antibiotics, and then replica plated to medium containing ampicillin to identify clones that have lost the recombinant plasmid derived from pUC18 which confers resistance to ampicillin.

After isolating and characterizing a deletion mutant, it may be advantageous to place a Tn10 adjacent to the deletion so that the deletion can be moved into other strains. For example, the zhf-2::Tn10 insertion in the *E. coli* K-12 strain Chi6096 (Table 1) can be transduced using standard transduction procedures for P1L4 to introduce the transposon into a great diversity of bacterial strains and species that are transducible with the wide host range generalized transducing phage P1L4. Since tetracycline resistance is associated with sensitivity to fusaric acid, one can take a P1L4 lysate grown on a strain carrying a delta-asd mutation, for example, Chi2984 (Table 1) and transduce any recipient strain with zhf-2::Tn10, followed by selection for fusaric acid resistance. In this case, the delta-asd mutation replaces the zhf-2::Tn10. If the recipient strain has a different restriction behavior than *E. coli* K-12, this barrier may be eliminated by subjecting the recipient strain to a brief heat shock, for example, 5 to 10 min. at 45°–50° C.

An analogous method can be used for isolating delta-asd mutants of various strains of *S. typhimurium*. The generalized transducing phage P22HT int can be grown on strains such as, for example, Chi3013, Chi3536, or Chi3537, which possess zhf-1::Tn10, zhf-4::Tn10, and zhf-3::Tn10, respectively (see Table 1). The phage carrying the transposon is then used to transduce other suitable recipient strains to tetracycline resistance. A P22HT int lysate, resulting from propagation of the phage on a bacterial strain carrying a delta-asd mutation, for example Chi3021 or Chi3628, is used to transduce a strain carrying a zhf::Tn10 insertion. Mutants which are resistant to fusaric acid are selected. Similar to the case in *E. coli*, the delta-asd mutation replaces the inserted Tn10.

It should be noted that transduction to insert delta-asd mutations as replacements for a zhf::Tn10 insertion, with selection of the desired transductant by its resistance to fusaric acid occurs at a frequency of $10^{-4}$–$10^{-5}$, whereas spontaneous loss of the Tn10 insert by a deletion type mutational event occurs at a frequency of about $10^{-8}$. Thus the use of transduction with a phage carrying a delta-asd gene in the construction of the desired strains ensures the correct genotype with a very low probability for a recovery of new deletion mutants.

Many strains of Salmonella are not transducible with phage P22. Two of the Tn10 insertions linked to the asd gene, the delta-asdA13 mutation and the delta-asdA4 mutation linked to zhf-4::Tn10 have been placed in Salmonella strains that possess a galE mutation. When these strains, Chi3629, Chi3638, Chi3630 and Chi3656, respectively, are grown in the presence of galactose they have a normal smooth lipopolysaccharide coat (LPS) and are sensitive to P22. However, growth in the absence of galactose causes the cells to have a rough coat lacking LPS side chains; cells grown in the absence of galactose are infectible by P1L4. P1L4 can be propagated on Chi3629 (Table 1), and the lysate used to transduce a P1L4 sensitive strain, resulting in a zhf-3::Tn10 insertion into the strain. P1L4 propagated on Chi3630, which has the delta-asdA13 mutation, is used to transduce the Tn10 carrying strain, and fusaric acid resistant cells are selected. The result is the introduction of the delta-asdA13 mutation into a new Salmonella species. Alternatively, P1L4 can be propagated on Chi3656 and a suitable recipient transduced to $Tc^r$ in the presence of DAP. In this way the delta-asdA4 mutation can be inherited linked to zhf4::Tn10. The zhf-4::Tn10 can then be removed by transduction with P1L4 grown on Chi3385 (Table 1) and used to transduce to $Tc^s$ by selecting for fusaric acid resistance.

If transduction of one of the available asd deletion mutations into a species or strain of choice is not feasible or possible, then the strategy described above for isolation of asd mutants can be employed. A bacterial strain is mutagenized, and mutant enrichment and selection is carried out in the presence of DAP to selectively isolate mutants unable to synthesize homoserine. After obtaining an asd mutation, the reversion frequency of the mutant is determined. If a deletion mutation is desired, it can be done in a variety of ways known in the art, but most simply by introducing a Tn10 transposon library by transduction, selecting for a simultaneous $Asd^+$ and $Tc^r$ phenotype. Generally, the Tn10 will be closely linked to the asd gene, and if fusaric acid resistant isolates are selected, deletion of the Tn10 and the adjacent DNA into the asd gene will result in an asd deletion mutation. If the Tn10 procedure does not provide results in a bacterial species, then another transposon can be used to establish linkage to the asd gene; available transposons are known in the art (see Buhkari et al). The transposon-asd gene complex can be cloned using known genetic engineering techniques. A recombinant can be prepared with precise deletion of the asd gene, the deleted asd gene can then be returned to the wild-type bacterial strain, as described above.

Another characteristic of the host cells of the invention is that they have been transformed with a recombinant polynucleotide construct encoding two genes. The first recombinant gene encodes a polypeptide which functionally replaces the enzymatic activity of the inactive native gene. For example, an $Asd^-$ E. coli cell may be transformed with a recombinant polynucleotide construct encoding the asd gene from S. mutans. Evidence that the S. mutans asd gene product functionally replaces the E. coli gene product was presented by Curtiss et al (1982). Moreover, the S. mutans gene also exemplifies another characteristic necessary for the first recombinant gene, i.e., it does not normally recombine with the E. coli gene because of a lack of sequence homology. The S. mutans asd gene sequence, and its lack of homology to the E. coli sequence was reported in Cardineau and Curtiss (1987). This lack of recombination between the host cell gene and the recombinant gene is required to maintain the linked selective pressure for the second recombinant gene. One can, however, use an asd gene cloned from the desired recipient strain provided that the recipient host has some or all of the nucleotide sequence of the $asd^+$ gene and/or flanking sequences deleted so that double crossover recombination with the cloned asd gene in the vector is not possible. Examples of this include the use of the S. typhimurium asd gene as contained in the vector pYA292 and contained in a variety of E. coli and/or S. typhimurium strains with delta-asd strains which lack any and all nucleotide sequences contained on pYA292; and a system in which the deletion is partial for the asd structural gene, but extends into its flanking regions. Other examples of genes which can complement an asd mutation are known in the art, and include, for example, the asd gene from B. lactofermentum (Marquez et al (1985)). The construction of vectors containing the asd gene from S. mutans, which can be used to transform asd strains of E. coli and S. typhimurium are discussed in the Examples, infra, and include pYA248 and pYA 292. Table 1 lists bacterial strains and Table 2 (shown in Example 10) lists strains and plasmids for plasmid constructions.

The second recombinant gene in the polynucleotide sequence encodes that of a desired polypeptide, for example, a viral or bacterial or fungal or parasite antigent a commercially desirable enzyme or polypeptide, etc., the expression of which may be dependent in a control sequence linked to the first gene. This linkage may result from the orientation of the two genes in the vector, so that both genes could be, for example, under the control of the same control elements, for example, the same promoter and operator. Methods of constructing vectors with these characteristics are known in the art using recombinant DNA technology and are discussed more fully in the section on vaccines, infra. Examples of vectors in which the second gene encodes beta-galactosidase, surface protein antigen A (SpaA) of S. Mutans, and antigens from M. leprae are presented infra, in the Examples section. Included in the Examples section also are expression vectors which contain the S. mutans asd gene or the S. typhimurium asd gene which are useful for complementing the $Asd^-$ phenotype in S. typhimurium and in E. coli.

Another embodiment of the invention is the use of the host cells of the invention in a method for the production of desired polypeptides. Cell growth conditions depend upon the genus and strain of the host cell selected, and are known in the art. However, the cells are grown in an environment in which the loss of the recombinant gene whose products functionally complements the missing enzyme in cell wall production causes cell lysis. For example, if the host cell is an $asd^-$ mutant of E. coli or S. typhimurium, the cells containing the recombinant asd gene operationally linked to the second recombinant gene are grown in an environment that lacks DAP but contains homoserine or threonine and methionine. Loss of the recombinant asd gene causes a reversion to the $DAP^-$ phenotype, and continued growth in the absence of DAP causes cell lysis.

Another embodiment of the invention is for use as bacteria designed for release into the environment to product pesticides, fungicides, etc. or to degrade toxic pollutants wherein the recombinant genes specifying the pesticide, fungicide or toxic waste degrading enzyme(s) are linked to a recombinant gene whose product functionally complements a mutation of the bacterium causing absence of an enzyme essential for cell wall production. Since this constitutes a balanced lethal, only bacteria expressing the desired trait will survive and reproduce thus ensuring continued production of the pesticide, fungicide, etc. or enzyme degrading toxic wastes.

A further embodiment of the invention is to use the construction of the balanced lethal arrangements of a mutation in the chromosome blocking synthesis of a unique essential constituent of the cell wall with a wild-type nonhomologous gene complementing that defect and linked to a gene specifying production of a valuable product useful in medicine, industry or agriculture. In such cases, the balanced lethal construct would most likely be grown using fermentation technology.

The host cells of the invention are also useful as constituents of live vaccines, in which case the second recombinant gene would encode an antigen of a fungal, bacterial, parasitic, or viral disease agent. Live vaccines are particularly useful where local immunity is important and might be a first line of defense. However, in this case it is essential that the host cells be nonpathogenic to the individual being vaccinated. Examples of cells from which suitable host cells may be derived by insertion of, for example, an asd mutation and subsequent transformation by a polynucleotide containing the two recombinant genes, described above, are the delta-cya delta-crp mutants described in Curriss and Kelly (1987).

Once rendered avirulent by, for example, the introduction of the delta-cya delta-crp mutations, the microbes can serve as the immunogenic component of a vaccine to induce immunity against the microbe. Thus, the use of any microbe possessing the characteristics of the host cells described supra, including non-pathogenicity, are contemplated by this invention, including but not limited to Salmonella, *E. coli* —*S. typhimurium* hybrids, Shigella, Yersinia, Pasteurella, Legionella or Brucella. Preferred microbes are members of the genus Salmonella such as *S. typhimurium, S. typhi, S. paratyphi, S. gallinarum, S. enteritidis, S. choleraesius, S. arizona,* or *S. dublin.*

In another embodiment of the invention, the avirulent derivative of a pathogenic microbe also referred to herein as a carrier bacterium can be used to deliver selected antigens to the GALT, for example to the Peyer's patches of the ileum. Some genera of bacteria, such as Salmonella, are known to home to the Peyer's patches (Carter, P. B. and F. M. Collins, J. Exp. Med. 139:1189 (1974)). *S. typhimurium—E. coli* hybrids have also been shown to colonize Peyer's patches in mice (Hohmann, A. W., et al, Infect. and Immun. 22:763 (1978)). If these carrier bacteria contain and express a recombinant gene from a pathogenic organism, antibodies against the antigenic gene product produced from the pathogen will be induced. With the advent of recombinant DNA techniques, it now becomes possible to develope totally unique vaccines in which specific antigens are produced, not by the etiologic agent, but by another host strain of bacteria capable of expressing the gene for that antigen. It is also possible, when antigens might cross-react with an antigen of the mammalian host and thus potentiate the induction of autoimmunity, to use recombinant DNA techniques to alter the gene so that the affecting cross-reacting antigenic determinant is not produced. Thus, recombinant DNA techniques can be employed to develop vaccines that do not have any material capable of cross-reacting with vertebrate host antigens or capable of eliciting an autoimmune state.

It is apparent that the present invention has wide applicability to the development of effective vaccines against bacterial, fungal, parasite or viral disease agents where local immunity is important and might be a first line of defense. Some examples are vaccines for the control of pneumonic plague caused by *Yersinia pestis,* of gonorrhea caused by *Neisseria gonorrhoeae,* of syphilis caused by *Treponema pallidum,* and of venereal diseases as well as eye infections caused by *Chlamydia trachomatis.* Species of Streptococci from both group A and group B, such as those species that cause sore throat or heart diseases, *Neisseria meningitidis, Mycoplasma pneumoniae, Hemophilus influenza, Bordetella pertussis, Mycobacterium tuberculosis, Mycobacterium leprae, Bordetella avium, Escherichia coli, Streptococcus equi, Streptococcus pneumoniae, Brucella abortus, Pasteurella hemolytica, Vibrio cholera, Shigella* species, and *Legionella pneumophila* are additional examples of bacteria within the scope of this invention from which genes could be obtained. Viral vaccines, such as those produced against influenza viruses, are also encompassed by this invention. Viral vaccines can also be produced against other viruses, either DNA or RNA viruses, for example from the classes Papovirus, Adenovirus, Herpesvirus, Poxvirus, Parvovirus, Reovirus, Picornavirus, Myxovirus, Paramyxovirus, or Retrovirus. Vaccines to protect against infection by pathogenic fungi, protozoa and parasites are also contemplated by this invention.

In a further embodiment when the immunogenic component of the vaccine is an allergen of the host such a vaccine may be used in an exposure regimen designed to specifically desensitize an allergic host.

In one of its embodiments, the invention can be described as a vaccine for the immunization of a vertebrate animal comprising a live avirulent derivative of a pathogenic microbe said derivative being substantially incapable of producing functional adenylate cyclase and AMP receptor protein while being capable of expressing a recombinant gene derived from an organism that is a pathogen of or that produces an allergen of said animal.

In yet another embodiment the avirulent microbes of this invention may be used as vectors for the synthesis of various host proteins. Because the avirulent microbes of this invention are able to traverse a variety of immunocompetent structures including GALT, mesenteric lymph nodes and spleen after introduction into the host, such microbes may be used to target a variety of immunoregulatory products. Accordingly, one or more genes encoding immunoregulatory proteins or peptides may be recombinantly introduced into the avirulent microbes such that when the microbes taking up residence in the appropriate immunocompetent tissue are capable of expressing the recombinant product to suppress, augment or modify the immune response in the host. Examples of immunoregulatory molecules include but are not limited to: colony stimulating factors (macrophage, granulocyte, or mixed), macrophage chemotoxin, macrophage inhibition factor, leukocyte inhibitory factors, lymphotoxins, blastogenic factor, interferon, and interleukins.

Each of the terms in these embodiments of the invention is analyzed in the following discussion.

By vaccine is meant an agent used to stimulate the immune system of a living organism so that protection against future harm is provided. Immunization refers to the process of inducing a continuing high level of antibody and/or cellular immune response in which T-lymphocytes can either kill the pathogen and/or activate other cells (e.g., phagocytes) to do so in an organism, which is directed against a pathogen or antigen to which the organism has been previously exposed. Although the phrase "immune system" can encompass responses of unicellular organisms to the presence of foreign bodies, e.g., interferon production, in this application the phrase is restricted to the anatomical features and mechanisms by which a multi-cellular organism produces antibodies against an antigenic material which invades the cells of the organism or the extra-cellular fluid of the organism. The antibody so produced may belong to any of the immunological classes, such as immunoglobulins A, D, E, G or M. Of particular interest are vaccines which stimulate production of immunoglobulin A (IgA) since this is the principle immunoglobulin produced by the secretory system of warm-blooded animals, although vaccines of the invention are not limited to those which stimulate IgA production. For example, vaccines of the nature described herein are likely to produce a broad range of other immune responses in addition to IgA formation, for example, cellular and humoral immunity. Immune response to antigens is well studied and widely reported. A survey of immunology is given in Barrett, James T., *Textbook of Immunology:* Fourth Edition, C. V. Mosby Co.,, St. Louis, MO (1983).

A vertebrate is any member of the subphylum Vertebrata, a primary division of the phylum Chordata that includes the fishes, amphibians, reptiles, birds, and mammals, all of which are characterized by a segmented bony or cartilaginous spinal column. All vertebrates have a functional immune system and respond to antigens by producing antibodies. Thus all vertebrates are capable of responding to vaccines. Although vaccines are most commonly given to mammals, such as humans or dogs (rabies vaccine), vaccines for commercially raised vertebrates of other classes, such as the fishes and birds if of the nature described herein, are within the scope of the present invention.

In one embodiment of the invention is the use of an avirulent derivative of a pathogenic microbe that homes to the GALT or BALT as a carrier of the gene product which is used for stimulating antibody response against a pathogen or allergen. Avirulent does not mean that a microbe of that genus or species can not ever function as a pathogen, but that the particular microbe being used is avirulent with respect to the particular animal being treated. The microbe may belong to a genus or even a species that is normally pathogenic but must belong to a strain that is avirulent. By pathogenic is meant capable of causing disease or impairing normal physiological functioning. Avirulent strains are incapable of inducing a full suite of symptoms of the disease that is normally associated with its virulent pathogenic counterpart. Microbes as used herein include bacteria, protozoa, and unicellular fungi.

Techniques for transferring genetic material from a first organism to a second organism which normally does not exchange genetic material with the first organism, have recently become widely available as the result of rapidly expanding recombinant DNA technology. In this application, genetic material that has been transferred from one organism into a second in such a manner that reproduction of the second organism gives rise to descendants containing the same genetic material is referred to as a recombinant gene. The term gene is being used here in its broadest sense to represent any biological unit of heredity. It is not necessary that the recombinant gene be a complete gene as present in the parent organism, which was capable of producing or regulating the production of a macromolecule, for example, a functioning polypeptide. It is only necessary that the gene be capable of serving as the template used as a guide in the production of an antigenic product. The product may be one that was not found in that exact form in the parent organism. For example, a functional gene coding for a polypeptide antigen comprising 100 amino acid residues may be transferred in part into a carrier microbe so that a peptide comprising only 75, or even 10, amino acid residues is produced by the cellular mechanism of the host cell. However, if this gene product is an antigen that will cause formation of antibodies against a similar antigen present in the parent organism, the gene is considered to be within the scope of the term gene as defined in the present invention. Alternatively, if the amino acid sequence of a particular antigen or fragment thereof is known, it is possible to chemically synthesize the DNA fragment or analog thereof by means of automated gene synthesizers or the like and introduce said DNA sequence into the appropriate expression vector. At the other end of the spectrum is a long section of DNA coding for several gene products, one or all of which can be antigenic. Thus a gene as defined and claimed here is any unit of heredity capable of producing an antigen. The gene may be of chromosomal, plasmid, or viral origin.

In order for the gene to be effective in eliciting an immune response, the gene must be expressed. Expression of a gene means that the information inherent in the structure of the gene (the sequence of DNA bases) is transformed into a physical product in the form of a RNA molecule, polypeptide or other biological molecule by the biochemical mechanisms of the cell in which the gene is located. The biological molecule so produced is called the gene product. The term gene product as used here refers to any biological product or products produced as a result of the biochemical reactions that occur under the control of a gene. The gene product may be, for example, an RNA molecule, a peptide, or a product produced under the control of an enzyme or other molecule that is the initial product of the gene, i.e., a metabolic product. For example, a gene may first control the synthesis of an RNA molecule which is translated by the action of ribosomes into an enzyme which controls the formation of glycans in the environment external to the original cell in which the gene was found. The RNA molecule, the enzyme, and the glycan are all gene products as the term is used here. Any of these as well as many other types of gene products, such as glycoproteins and polysaccharides, will act as antigens if introduced into the immune system of an animal. Protein gene products, including glycoproteins and lipoproteins, are preferred gene products for use as antigens in vaccines.

In order for a vaccine to be effective in producing antibodies, the antigenic material must be released in such a way that the antibody-producing mechanism of the vaccinated animal can come into play. Therefore the microbe carrier of the gene product must be introduced into the animal. In order to stimulate a preferred response of the GALT or BALT cells as discussed previously, introduction of the microbe or gene product directly into the gut or bronchus is preferred, such as by oral administration, gastric intubation or in the form of aerosols, although other methods of administering the vaccine, such as intravenous, intramuscular, subcutaneous injection or intramammary or intrapenial or vaginal administration, is possible.

When the avirulent microbe is used, as a carrier microbe and once the carrier microbe is present in the animal, the antigen needs to become available to the animal's immune system. This may be accomplished when the carrier microbe dies so that the antigen molecules are released. Of course, the use of "leaky" avirulent mutants that release the contents of the periplasm without lysis is also possible. Alternatively, a gene may be selected that controls the production of an antigen that will be made available by the carrier cell to the outside environment prior to the death of the cell.

The use of the avirulent strain with asd mutations and occasional loss of the Asd$^+$ cloning vector would permit lysis of approximately 1% of the bacteria during each generation (see examples) to release the cell contents to thus stimulate an immune response against the released cell contents including any colonization and virulence antigens.

The use of pathogens to deliver antigens from other pathogens to the GALT or BALT would be inappropriate if it were not for the fact that such pathogens can be rendered avirulent while retaining ability to invade Peyer's patches or the BALT.

The organism from which the recombinant gene is derived may be any pathogen of the animal being vaccinated or may be an organism that produced an allergen or other antigen of the animal. Allergens are substances that cause allergic reaction, in this case in the animal which will be vaccinated against them. Many different materials may be allergens, such as animal dander and pollen, and the allergic reaction of individual animals will vary for any particular allergen. It is possible to induce tolerance to an allergen in an animal that normally shows an allergic response. The methods of inducing tolerance are well-known and generally comprise administering the allergen to the animal in increasing dosages. Further discussion of tolerance induction is given in the Barrett textbook previously cited. Lastly the host organism itself can serve as a source of genetic material when immunoregulatory genes are being expressed by the vectors.

Administration of a live vaccine of the type disclosed above to an animal may be by any known or standard technique. These include oral ingestion, gastric intubation, or broncho-nasal spraying. All of these methods allow the live vaccine to easily reach the GALT or BALT cells and induce antibody formation and are the preferred methods of administration. Other methods of administration, such as intravenous injection, that allow the carrier microbe to reach the animal's blood stream may be acceptable. Intravenous, intramuscular or intramammary injection are also acceptable with other embodiments of the invention, as is described later.

Since preferred methods of administration are oral ingestion, aerosol spray and gastric intubation, preferred carrier microbes are those that belong to species that home preferentially to any of the lymphoepithelial structures of the intestines or of the bronchii of the animal being vaccinated. These strains are preferred to be avirulent derivatives of enteropathogenic strains produced by genetic manipulation of enteropathogenic strains. Strains that home to Peyer's patches and thus directly stimulate production of IgA are most preferred. In animals these include specific strains of Salmonella, and Salmonella—*E. coli* hybrids that home to the Peyer's patches.

Recombinant DNA techniques are now sufficiently well known and widespread so as to be considered routine. In very general and broad terms, this method consists of transferring the genetic material, or more usually part of the genetic material, of one organism into a second organism so that the transferred genetic material becomes a permanent part of (recombines with) the genetic material of the organisms to which it is transferred. This usually consists of first obtaining a small piece of DNA from the parent organism either from a plasmid or a parent chromosome. A plasmid (also called an extrachromosomal element) is a hereditary unit that is physically separate from the chromosome of the cell. The DNA may be of any size and is often obtained by the action of a restriction endonuclease enzyme which acts to split DNA molecules at specific basepair sites. Following ligation to plasmid, phage or cosmid vectors to form recombinant molecules the recombinant molecules may be transferred into a host cell by various means such as transformation (uptake of naked DNA from the external environment, which can be artificially induced by the presence of various chemical agents, such as calcium ions). Other methods such as transduction are also suitable, wherein the recombinant DNA is packaged within a phage such as transducing phage or cosmid vectors. Once the recombinant DNA is in the carrier cell, it may continue to exist as a separate piece (generally true of complete transmitted plasmids) or it may insert into the host cell chromosome and be reproduced with the chromosome during cell division.

Derivatives of avirulent microbes are also contemplated to be within the scope of this invention. By derivative is meant sexually or asexually derived progeny and mutants of the avirulent strains including single or multiple base substitutions, deletions, insertions or inversions which retain the inability to produce functional adenylate cyclase and AMP receptor protein with or without naturally occurring virulence plasmids. For example, strains such as Chi4062 and Chi4064 carry the gyra mutation conferring nalidixic acid resistance which has been used herein as a convenient marker. However, drug resistance is not a desirable attribute for strains to be used as vaccines. Thus the gyrA mutation can be easily removed by transducing the $gyrA^+$ (conferring sensitivity to nalidixic acid) gene into strains by selecting for inheritance of a closely linked Tn10 and then removing Tn10 by selection for fusaric acid resistance (see examples).

The dosages required will vary with the antigenicity of the gene product and need only be an amount sufficient to induce an immune response typical of existing vaccines. Routine experimentation will easily establish the required amount. Typical initial dosages of vaccine could be 0.001–0.1 mg antigen/kg body weight, with increasing amounts or multiple dosages used as needed to provide the desired level of protection.

The pharmaceutical carrier in which the vaccine is suspended or dissolved may be any solvent or solid or encapsulated in a material that is non-toxic to the inoculated animal and compatible with the carrier organism or antigenic gene product. Suitable pharmaceutical carriers include liquid carriers, such as normal saline and other non-toxic salts at or near physiological concentrations, and solid carriers not used for humans, such as talc or sucrose, also feed for farm animals. Adjuvants may be added to enhance the antigenicity if desired. When used for administering via the bronchial tubes, the vaccine is preferably presented in the form of an aerosol.

Immunization with a pathogen derived gene product can also be used in conjunction with prior immunization with the avirulent derivative of a pathogenic microorganism acting as a carrier to express the gene product specified by a recombinant gene from a pathogen. Such parenteral immunization can serve as a booster to enhance expression of the secretory immune response once the secretory immune system to that pathogen-derived gene product has been primed by immunization with the carrier microbe expressing the pathogen derived gene product to stimulate the lymphoid cells of the GALT or BALT. The enhanced response is known as a secondary, booster, or anamnestic response and results in prolonged immune protection of the host. Booster immunizations may be repeated numerous times with beneficial results.

The above disclosure generally describes the present invention. A more complete understanding can be obtained by reference to the following specific examples which are provided herein for purposes of illustration only and are not intended to be limiting unless otherwise specified.

Deposits of Strains Useful in Practicing the Invention

A deposit of biologically pure cultures of the following strains were made with the American Type Culture Collection, 12301 Parklawn Drive, Rockville, Md. The accession number indicated was assigned after successful viability testing, and the requisite fees were paid. Access to said cultures will be available during pendency of the patent application to one determined by the Commissioner to be entitled thereto under 37 CFR 1.14 and 35 USC 122. All restriction on availability of said cultures to the public will be irrevocably removed upon the granting of a patent based upon the application. Moreover, the designated deposits will be maintained for a period of thirty (30) years from the date of deposit, or for five (5) years after the last request for the deposit; or for the enforceable life of the U.S. patent, whichever is longer. Should a culture become nonviable or be inadvertently destroyed, or, in the case of plasmid-containing strains, loose its plasmid, it will be replaced with a viable culture(s) of the same taxonomic description.

| Strain | Deposit Date | ATCC No. |
| --- | --- | --- |
| Chi6097 containing pYA232 | Oct. 6, 1987 | 67,537 |
| Chi2978 | Oct. 6, 1987 | 53,679 |
| Chi3520 | Oct. 6, 1987 | 53,681 |
| Chi4072 containing pYA248 | Oct. 6, 1987 | 67,538 |
| Chi3008 | Oct. 6, 1987 | 53,680 |
| Chi2108 | Oct. 6, 1987 | 53,678 |
| Chi6097 containing pYA292 | Sept. 26, 1988 | 67,813 |

Described below are examples of the present invention which are provided only for illustrative purposes, and not to limit the scope of the present invention. In light of the present disclosure, numerous embodiments within the scope of the claims will be apparent to those of ordinary skill in the art.

Examples

1. Isolation of asd⁻ Mutants

Mutants are isolated which are auxotrophic for homoserine or threonine and methionine in the presence of DAP. (The biosynthetic pathways are shown in FIG. 1.) There are two genes specifying two different homoserine dehydrogenases capable of converting beta-aspartate semi-aldehyde to homoserine, and since double mutational events are exceedingly rare, all such homoserine requiring mutants invariably also require DAP due to a single mutation causing a specific defect in the asd gene. The selection procedure is based upon the discovery that the presence of DAP in the mutagenesis and selection media allows depletion of homoserine and its products, methionine and threonine, causing cessation of protein synthesis in the mutants, rendering them insensitive to antibiotics which inhibit cell wall synthesis. In contrast, wild-type cells continue protein synthesis, and thus are sensitive to these antibiotics.

Broth grown cultures of prototrophic E. coli K-12 strain, Chi289, and a wild-type prototrophic S. typhimurium strain, Chi3000, are inoculated into separate flasks containing a mineral salts medium supplemented with 0–5% glucose as an energy source. Any of the minimal media whose formulae are described by Miller (1972) are satisfactory. The cultures are grown with aeration to a density of approximately $5 \times 10^8$ cells per ml.

The culture is mutagenized to enhance the frequency of asd⁻ mutants. Mutagenesis is by chemical methods, such as with nitrous acid, or by ultraviolet irradiation. Both types of techniques are described by Miller (1972). Alternatively, transposon-induced mutagenesis may be used. Transposon techniques for mutagenesis are reviewed in Kleckner et al (1977). When mutagenesis is completer the medium is supplemented with 60 micrograms L-homoserine per ml, and 50 micrograms of meso-DAP per ml. The cells in culture are grown with aeration for approximately 10 generations to permit all mutant cells to become homogeneous with regard to the mutant genotype and to fully express the mutant phenotype. A total of $1.0 \times 10$ cells from each mutagenized culture are collected by filtration on premoistened sterilized Millipore filters (0.45 micron pore size). The filters are not allowed to dry during filtration. The cells are then washed several times with prewarmed buffered saline with gelatin (BSG) containing DAP.

The filters are removed and each is placed in 20 ml of synthetic mineral salts medium supplemented with 50 micrograms of meso-DAP per ml and 0.5% glucose. The cultures, which are contained in 250 ml Erlenmeyer flasks, are incubated at 37° C. with aeration by rotary shaking. The cultures are grown for a time sufficient to allow asd⁻ mutants to exhaust their internal supplies of homoserine and its derivative amino acids, threonine and methionine, i.e., approximately one hour. During this 1 hour period of growth the culture should change from approximately $5 \times 10^6$ cells/ml to approximately $1 \times 10^7$ cells per ml. The cells should not be allowed to grow to higher density since wild-type cells will lyse during the selection procedure, releasing threonine and methionine, which can then serve as substrates for protein synthesis in the mutant asd⁻ cells. However, the concentrations of amino acids released from $10^7$ cells are insufficient to support growth of these mutants.

Selection for mutants is in the presence of D-cycloserine and ampicillin. D-cycloserine, prepared at 50 mg/ml in pH 8.0 phosphate buffer (Curriss et al, 1965) and ampicillin, prepared at 50 mg/ml in sterile water, are added to 20 ml of culture to give final concentrations of 100 micrograms/ml and 50 micrograms/ml of D-cycloserine and ampicillin, respectively. The culture is grown with aeration at 37° C. for approximately three hours. During this time, the D-cycloserine and ampicillin act synergistically to inhibit cell wall synthesis in growing but not in nongrowing cells. Surviving cells are then collected on a sterile pre-wetted Millipore filter (0.45 micron pore diameter), and washed free of the antibiotics with pre-warmed BSG containing DAP. The filter is transferred to a flask containing 20 ml of mineral salts medium supplemented with homoserine, DAP, and glucose, and allowed to grow overnight in a rotary shaker at 37° C. The ampicillin-cycloserine enrichment procedure can be repeated. After both selection rounds, suitable dilutions of the bacterial suspension are plated either on a mineral salts medium containing glucose as a carbon source and supplemented with homoserine and DAP, or on a complex agar medium, L-agar or Pennassay agar, supplemented with 50 micrograms of DAP/ml. The dilutions of the cultures are selected to yield 100–200 colonies per plate. The plates are incubated until the colonies are 2 to 3 mm in diameter, usually overnight incubation is sufficient, and are then replica plated to agar medium which lacks DAP, upon which asd⁻ mutants will not grow. Colonies growing on the master plate, but not the replica plate, are picked, purified, inoculated in medium containing DAP, and grown to approximately $10^8$ cells/mi. The putative mutants are tested for auxotrophy for DAP and homoserine, or DAP and methionine and threonine. In addition, the mutants are tested for an obligate requirement for DAP that cannot be supplied by L-lysine. E. coli asd⁻ mutant Chi2108 (Table 1) and S. typhimurium asd⁻ mutant Chi3008 were isolated using the above described procedure. Mutants induced and isolated by the above procedure may contain either point or deletion mutations.

2. Evaluation of the Genetic Stability of asd⁻ Mutants

Deletion mutations in the asd gene are essentially non-reverting, while point mutations are revertible. The genetic stability of the mutants isolated by the procedure in Example 1 is evaluated as follows.

The mutant cells are grown in 20 ml cultures to a density of approximately $2 \times 10^9$ cells/ml. The cultures are concentrated approximately 50 fold by centrifugation, and 100 microliter aliquots of undiluted, and of dilutions of $10^{-1}$, $10^{-2}$, and $10^{-3}$ are plated on agar, i.e., Penassay or L-agar or mineral salts agar with glucose, lacking DAP. Spontaneous reversion of mutants is determined by incubating one set of the plates at 37° C. for two days. UV induced reversion is determined by exposing another set of the plates to approximately 1.5 Joules per meter square of Uv irradiation, followed by incubation in the dark for two days; incubation in the dark precludes photoreactivation of the UV induced mutations. Reversion is determined by the loss of auxotrophy for DAP and for homoserine or threonine and methionine.

Using the above procedure it was determined that Chi2108, the E. coli asd mutant is essentially non-reverting; therefore, it contains a deletion mutation. In contrast, the S. typhimurium asd mutant Chi3008 does revert, as a result of its point mutation.

3. Construction of Libraries of Tn10 Insertions in S. typhimurium

Tn10 is 9.2 kb in size, therefore, it can be accommodated only in bacteriophage transposon insertion vectors which have considerable nonessential phage genes deleted, an example of which is the bacteriophage lambda Tn10 transposon vector, NK561, constructed by Kleckner et al (1977). S. typhimurium is naturally resistant to bacteriophage lambda. However, it can be rendered sensitive by introduction of the E. coli K-12 lamb gene which encodes the outer membrane protein receptor for lambda attachment, and by inclusion of a galE mutation, which causes a rough coat due to elimination of lipopolysaccharide. Thus, transposon libraries of random Tn10 insertions in the chromosome of S. typhimurium can be prepared by infection of either DB4673 or Chi3477 with lambda-NK561, using the following procedure. (See Table 1 for the description and derivation of both strains.)

Overnight cultures of the strain are grown in lambda broth or L-broth lacking glucose but containing 0.2% maltose to induce expression of lamB. When the culture reaches approximately $3 \times 10^8$ cells/ml, lambda-NK561 is added at a concentration of $1.0 \times 10^9$ phage/ml, i.e., at a m.o.i. of about 3 phage per bacterium. Lambda phage does not replicate in S. typhimurium, therefore, a higher multiplicity of infection can be used than in E. coli, since lambda infection does not cause death of the infected S. typhimurium cells. After incubation at 37° C. for a time sufficient to allow the Tn10 to transpose from the lambda phage genome to various sites in the S. typhimurium genome, generally 60 to 90 minutes, aliquots of undiluted and 10-fold diluted suspensions are plated directly on L. or Penassay agar containing 12.5 micrograms tetracycline/ml. The plates are incubated overnight at 37° C., 1–2 ml of broth are added to each of approximately 10 plates, and the colonies are resuspended using a sterile glass spreader. Cells in the suspension are collected by centrifugation, washed, and resuspended in 1% peptone plus 5% glycerol. The library is stored at −70° C.

4. Preparation of Phage P22 Lysates of the Tn10 Transposon Library

The movement of transposons in S. typhimurium generally requires the use of the generalized Salmonella transducing phage, P22. Lysates of the high frequency transducing phage, P22HT intr on the Tn10 transposon libraries constructed in DB4673 and Chi3477, as described in Example 3, are prepared as follows.

Overnight cultures of the transposon libraries in DB4673 and Chi3477 are grown in Luria broth. Each culture is diluted 100-fold in Luria broth, and grown with aeration for 2–3 hours at 37° C. to obtain an exponentially growing culture at approximately $3 \times 10^8$ cells/ml. P22HT int is added at a m.o.i. of 3 phage/cell, and the mixture is incubated with aeration by rotary shaking at 37° C. for 90 minutes, after which, a small amount of chloroform is added to the cell suspension to facilitate lysis and/or death of remaining viable cells. Following an additional 10 minute incubation with aeration at 37° C., the lysate is centrifuged at 7,000 RPM for 10 minutes in a Sorvall refrigerated centrifuge to remove unlysed bacteria and bacterial debris. The supernatant is gently decanted, and stored in the presence of a few drops of chloroform at 4° C.

5. Creation and Selection of S. typhimurium Strains in which Tn10 is Closely Linked to the asd Gene.

Figure 2:
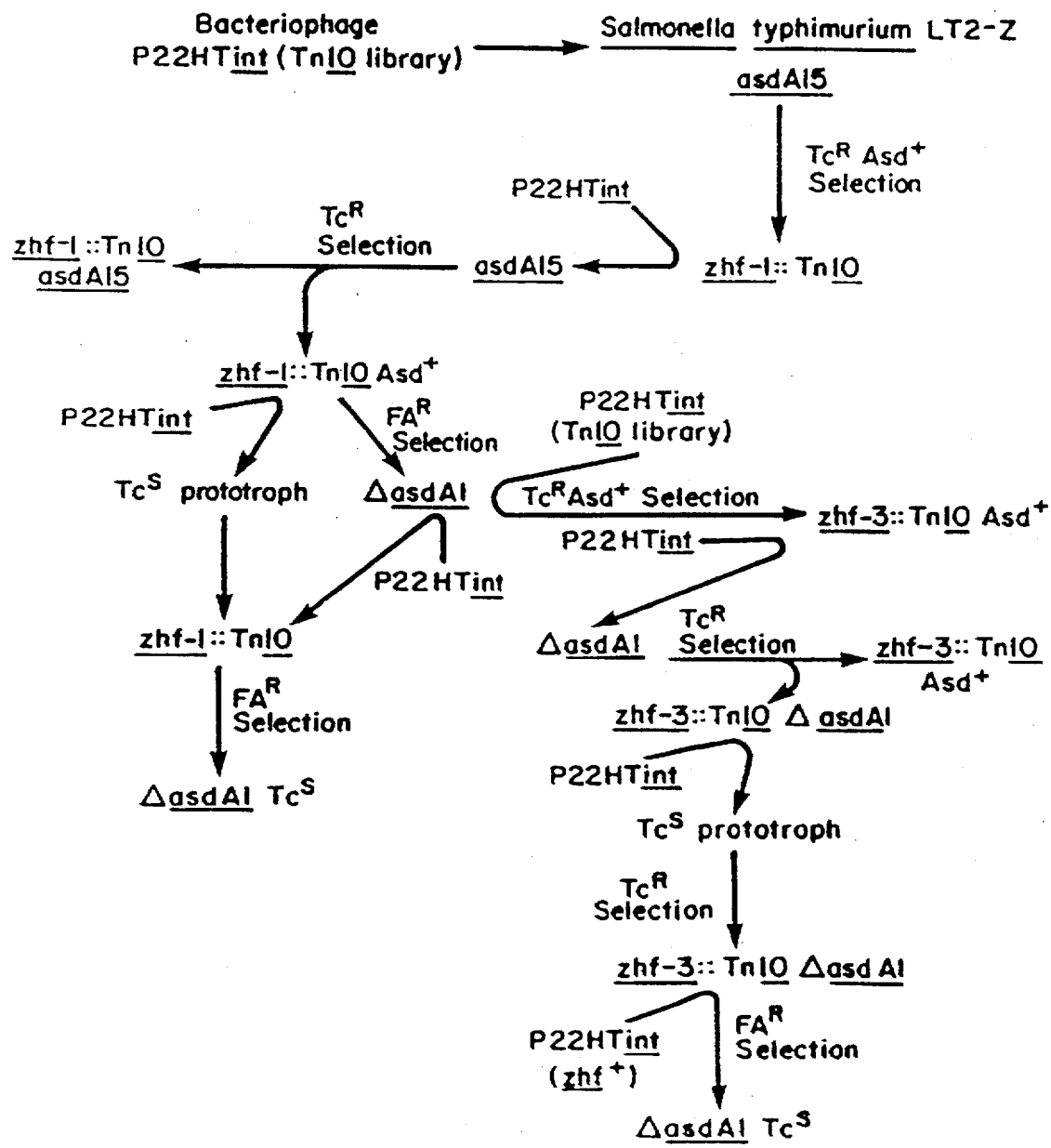
FIG. 2 is a flow chart for the creation of delta-asd mutants of Salmonella.

Strains in which Tn10 is closely linked to the asd gene are useful for the preparation of delta-asd mutants, and may be prepared and isolated as follows. A flow chart for creating delta-asd mutants is shown in FIG. 2, in which strains which may be utilized for the creation of the mutants are indicated in parentheses.

The S. typhimurium strain Chi3008, which contains an asdA15 point mutation, is incubated overnight at 37° C. in Luria broth containing 50 micrograms DAP/ml. The overnight culture is diluted 100-fold in fresh medium, and incubated until a titer of $3 \times 10^8$ cells/ml is achieved (generally, 2–3 hours). P22HTint, propagated on a S. typhimurium strain carrying a Tn10 library prepared in DB4673 or Chi3477, as described in Example 4, is added at a m.o.i. of approximately 0.3 (i.e., a titer of $1.0 \times 10^8$ phage/ml). After a 20 minute incubation to allow phage attachment and injection, 100 microliter aliquots of undiluted, 10-fold diluted, and 100-fold diluted cell suspensions are plated on either Penassay or L-agar lacking DAP and containing 12.5 micrograms tetracycline per ml. The plates are incubated overnight at 37° C.

Very rare $Tc^r$ $Asd^+$ transductants are observed. These transductants result from either two independent events, i.e., transduction of $Asd^-$ to $Asd^+$ and transduction of Tn10 at another chromosomal site, or a single event in which Tn10 is transduced adjacent to the $asd^+$ gene. Single events occur much more frequently than double events; thus, the vast majority of $Tc^r$ $Asd^+$ transductants will have a Tn10 closely linked to the asd gene. Several $Tc^r$ $Asd^+$ colonies are picked, colony purified, and cultures prepared.

P22HTint lysates are propagated on each $Tc^r$ $Asd^+$ transductant, using the methods described in Example 4, but substituting the $Tc^r$ $Asd^+$ cultures for the cultures described therein. Each lysate is then used to transduce a culture of Chi3008 growing in Luria broth, supplemented with 50 micrograms of DAP/ml. The transduced strains are plated on Penassay agar either lacking DAP or containing DAP and 12.5 micrograms tetracycline/ml In the former case, $Asd^+$ transductants are selected; in the latter case, the selection is for $Tc^r$ transductants inheriting a Tn10. Approximately 50 transductants are taken from each selection and evaluated for cotransduction of the other trait. If the Tn10 and $asd^+$ are linked, a high frequency of $Asd^+$ transductants should be tetracycline resistant, and vice versa. The frequency of co-transduction can be used to estimate the closeness of the Tn10 and $asd^+$ gene.

This procedure was used to isolate Chi3013, (FIG. 2) which is a $Tr^r$ $Asd^+$ transductant of Chi3008 (See Table 1).

6. Creation and Isolation of S. typhimurium Strains which have a Tn10 Generated delta-asd Gene.

The insertion of Tn10 into cells causes fusaric acid sensitivity as well as tetracycline resistance. Cells which have lost Tn10, which occurs infrequently, become resistant to fusaric acid. Loss of Tn10 causes deletions in the adjacent DNA. Thus, loss of Tn10 which is inserted close to asd⁺ frequently causes a deletion in the asd gene.

An overnight culture is prepared of Chi3013 (see FIG. 2) which is a Tc$^r$ Asd$^+$ transductant, and the cells in an 8–10 ml aliquot, which are pelleted by centrifugation at 7,000 RPM for 10 mint are suspended in 200 microliters of L-broth. Various dilutions are plated on nutrient agar containing 50 micrograms DAP/ml, 6 micrograms fusaric acid/ml, and 12 micrograms of autoclaved chlorotetracycline/ml. After overnight incubation at 37° C., isolated colonies are picked, and purified on medium containing DAP and fusaric acid. Small cultures are prepared from the purified strains, and each is tested for inability to grow in the absence of DAP, and for sensitivity to tetracycline.

Validation that all vestiges of Tn10 have been lost, and that the DAP requirement is due to a nonreverting deletion mutation is obtained by examining whether the Tc$^s$ Asd$^-$ mutants are able to revert either to Tc$^r$ or to Asd$^+$. This may be accomplished as follows.

A 10–20 ml aliquot of culture in L-broth containing DAP is grown with aeration to high density, the cells are concentrated 50-fold by centrifugation, and suitable dilutions are plated either on. Penassay agar lacking DAP or on Penassay agar containing DAP and also containing 12–5 micrograms of tetracycline/ml. The plates are incubated 1–2 days at 37° C. In the absence of Tc$^r$ or Asd$^+$ colonies, there is presumptive evidence that the strain carries deletions of the Tn10 and the asd gene sequence. A representative strain satisfying these requirements is Chi3021 (see FIG. 2 and Table 1).

7. Creation and Isolation of *S. typhimurium* Strains with a Tn10 Adjacent to a delta-asd Gene.

The availability of strains with Tn10 adjacent to a delta-asd gene allows the deletion to be moved into other strains.

The strains are constructed as described in Example 5, except that Chi3021 is used as a recipient prior to the selection of Tc$^r$ Asd$^+$ transductants. See FIG. 2. Strains Chi3537 and Chi3536 (Table 1), which carry the Tn10 insertions zhf-3LLTn10 and zhf-4::Tn10, respectively, were constructed by this method.

Upon verifying that Tn10 is linked to the delta-asdA1 mutation, one can recover the transductant that is tetracycline-resistant, but which remains DAP requiring. An example is strain Chi3520 (Table 1), which possesses the delta-asdA1 mutation.

Transduction of Chi4064 (Table 1) with P22 which has been propagated on Chi3520 (Table 1), followed by selection for tetracycline resistance in the presence of DAP generated strain Chi4070 (Table 1). (See FIG. 2.)

Removal of the zhf-4::Tn10 from Chi4070 by selection for fusaric acid resistance resulted in Tc$^s$ asd$^-$ strains, one of which is Chi4072.

Alternatively, loss of the transposon can be caused by transduction with phage P22HTint propagated on a Tc$^s$ prototroph, such as Chi3000 (Table 1), followed by selection for fusaric acid resistance.

The above described process can be repeated, and new deletions of the asd gene associated with the deletion of Tn10's present in Chi3536 and Chi3537 can be isolated. Fusaric acid-resistant, Tc$^s$ delta-asd mutant strains isolated in this way are Chi3628 and Chi3647.

8. Isolation and Characterization of *E. coli* Strains with Deletions in the asd Gene, and with Tn10 Transposons Linked to the asd Gene.

The procedures for the isolation and characterization of these strains are similar to those described for the generation of Asd mutants of *S. typhimurium*. However, the lambda-NK561 transposon vector is used to infect the suppressor-free prototroph Chi2842. The lambda vector, because of amber mutations in the O and P genes for DNA replication, is unable to replicate in Chi2842. Thus, the only way that Tc$^r$ survivors can be generated is by transposition of the Tn10 from the lambda-NK561 genome to the *E. coli* K-12 chromosome.

The Tn10 library is used to propagate the generalized transducing phage P1L4, which, in turn, is used to transduce an *E. coli* strain such as Chi2637 (Table Transductants which are Tc$^r$ and Asd$^+$ are selected; an example of this type of transductant is Chi2978 (Table 1).

Strains in which Tn10 is adjacent to a delta-asd gene can also be isolated. For example, Tn10 was inserted adjacent to the delta-asdA4 mutation in Chi2637, yielding the strain Chi2979 (Table 1).

The delta-asdA4 mutation linked to zhf-2::Tn10 from Chi2981 (Table 1) can be moved by P1L4 transduction into other strains such as JM83 (Table 1) to yield Chi6096 (Table 1). Subsequent fusaric acid selection, which eliminates the Tn10, yields new delta-asd strains. Using this procedure, Chi6097 (Table 1) was isolated.

9. Alternate Means of Introducing delta-asd mutations into *E. coli* and *S. typhimurium* Strains.

In addition to generating asd deletions by selection for deletional loss of the Tn10 adjacent to an asd$^+$ gene (as used to generate the delta-asdA1 mutation in Chi3021 (Table 1), or by moving a specific asd mutation such as delta-asdA1 by cotransduction with a closely linked Tn10, such as zhf-4::Tn10 (as was used to construct Chi4070 from Chi3520, see Table 1), a third method for introducing delta-asd$^-$ mutations is also possible. See the box in FIG. 2. In this method, the Tn10 linked to asd is transduced into a target recipient strain and Tc$^r$ transductants are isolated. Tn10s linked to asd may be zhf-1::Tn10, zhf-3::Tn10, or zhf-4::Tn10. The new strain containing the Tn10 is transduced with phage lysate propagated on a strain with a delta-asd mutation, and transductants which are fusaric acid resistant in the presence of DAP are selected. The phage lysate used in this step may be propagated on strains with delta-asdA1, or delta-asdA13, or delta-asdA14. There are several copies of Tn10 per cell in broth grown cultures. Loss of all copies of the Tn10 is necessary prior to full phenotypic expression of fusaric acid resistance. Therefore, the transduced recipient must be grown for several generations prior to plating on selective agar medium containing DAP, fusaric acid, and autoclaved chlorotetracycline. This procedure, however, is quite efficient, and allows the Tn10 to be replaced in one step with a well characterized deletion mutation. It should be reiterated that replacement of a zhf::Tn10 insertion conferring tetracycline resistance by transduction will occur at a frequency of 10 to 10 whereas spontaneous loss of the Tn10 insertion occurs at a frequency of about 10$^{-8}$. Thus following transduction there is a 1000- to 10,000-fold higher probability for inserting a specific delta-asdA mutation rather than generating a spontaneously-occurring new delta-asdA mutation.

10. Construction of Cloning Vectors Which Contain the asd$^+$ Gene from *S. mutans*

Figure 3:
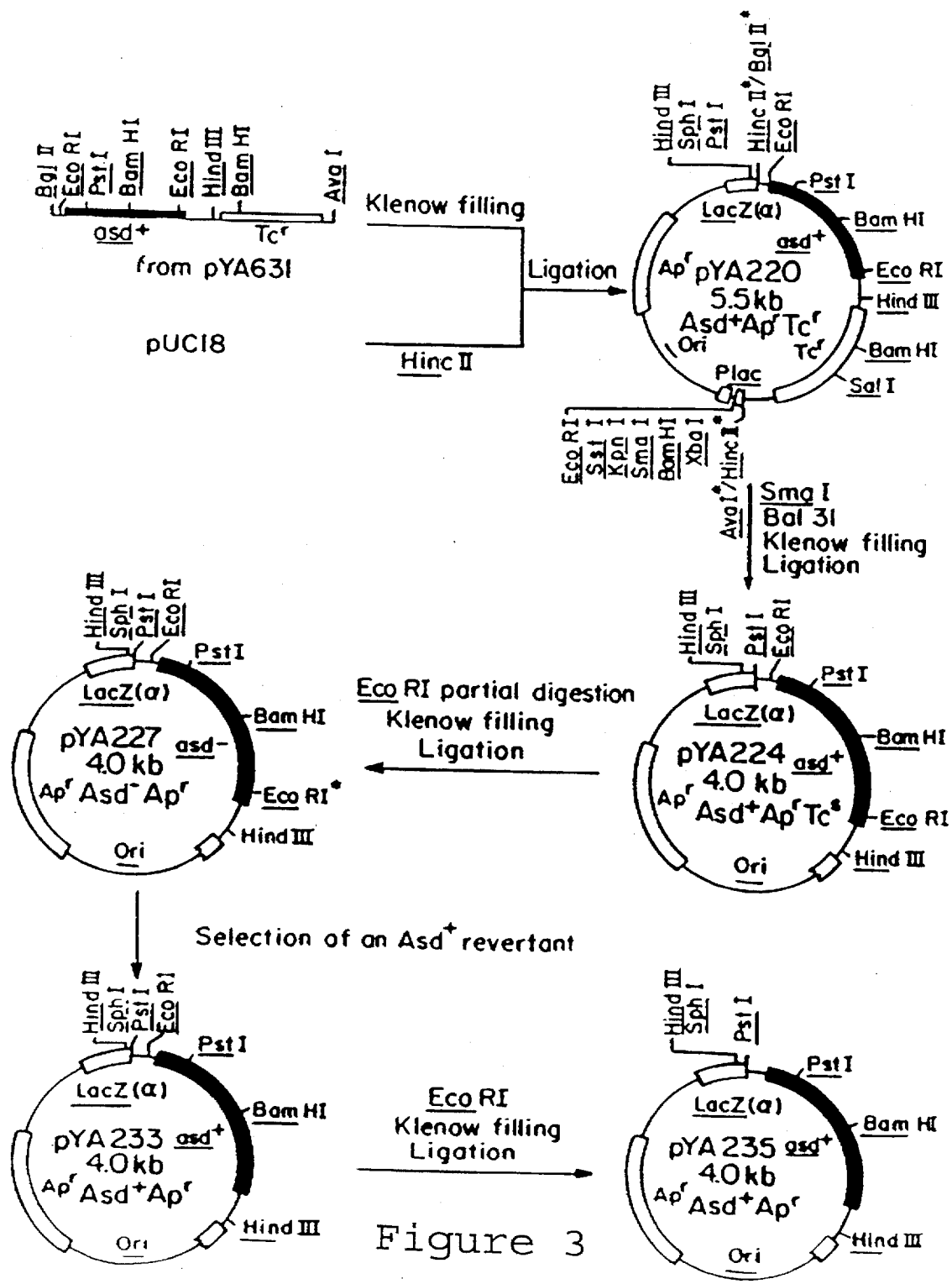
FIG. 3 is a flow chart which shows the significant features of the plasmids used in the construction of pYA235.

DAP requiring Asd$^-$ mutants, including delta-asd mutants, of *E. coli* and *S. typhimurium* can be converted to an Asd$^+$ phenotype by transformation with plasmids containing the asd$^+$ gene from *S. mutans*. Cloning vectors which contain this gene, into which a desired gene encoding a heterologous polypeptide can be inserted, are synthesized as follows (See FIGS. 3 and 4).

Unless otherwise indicated, standard techniques for recombinant DNA technology, for example, as described in Maniatis, Fritsch and Sambrook (1982) and DNA CLONING (1982) are used in the following constructions. The derivation, properties, and genotype of some of the plasmids used herein are given in Table 2. The abbreviations for restriction enzymes, and the DNA linkers for BglII and EcoRI are in Table 3.

TABLE 2

Plasmids

| Plasmid | Property | Derivation | Host strain number | Relevant genotype |
|---|---|---|---|---|
| pUC18 | 2.7 kb, multicloning sites, Ap$^r$ | Yanisch-Perron et al.[a] | JM83 | see Table 1 |
| pUC8-2 | 2.7 kb, multicloning sites, Ap$^r$ | Hanna et al.[b] obtained from Brousseau | CC118 | see Table 1 |
| pYA99 | 4.6 kb, P$_{trc}$ promoter, Ap$^r$ | constructed from pKK233-2 (Amann and Brosius[c]) by R. Goldschmidt | CC118 | see Table 1 |
| p15A | 2.25 kb, cryptic plasmid | obtained from S. S. Cohen via B. S. Strauss | X217 | E. coli 15 ΔthyA |
| pSC101 | 9.09 kb, low copy number, Tc$^r$ | obtained from S. S. Cohen | X2038 | E. coli K-12 T6$^x$ λ$^-$ T3$^r$ |
| pACYC184 | 4.0 kb, Cm$^r$, Tc$^r$ | Chang and Cohen[d] | X2230 | see Table 1 |
| pYA631 | 6.52 kb, Asd$^+$, Ap$^r$, Tc$^r$ | Cardineau and Curtiss[e] | X2984 | see Table 1 |
| F'(traD36 proA$^+$ proB$^+$ lacI$^q$ ΔM15)::Tn5 | | constructed by R. Goldschmidt | X6060 | same as CC118; see Table 1 |
| pYA232 | 10.19 kb, low copy number, lacI$^q$, Tc$^r$ | obtained by inserting the 1.1 kb EcoRI fragment of plasmid pAJC178 (Boulain et al[f]) containing the lacI$^q$ gene and its promoter into the unique EcoRI site of pSC101 | X6097 | see Table 1 |
| F'(traD36 proA$^+$ proB$^+$ lacI$^q$ΔM15) pSGMU37 | 7.6 kb, lacZ$^+$ | Errington[g] | X6054 | recA1 Δ(lac-pro) endA1 gyrA96 endA1 gyrA96 thi-1 hsdR17 supE44 relA1 |
| pYA177 | 6.3 kb, P$_{trc}$ promoter, overproduction of recombinant SpaA, Ap$^r$ | the PvuII-HindIII fragment of the spaA gene was inserted into plasmid pYA99. | CC118 | see Table 1 |

[a](1985) Gene 33:103–119;
[b](1984) Gene 30:247–250;
[c](1985) Gene 40:183–190;
[d](1978) J. Bacteriol. 134:1141–1156;
[e](1987) J. Biol. Chem. 262:3344–3353.;
[f](1986) Mol. Gen. Genet. 205:339–348;
[g](1986) J. Gen. Microbiol. 132:2953–2960.

TABLE 3

| | |
|---|---|
| BglII | Bg |
| AvaI | Av |
| HincII | Hc |
| SmaI | Sm |
| EcoRI | E |
| BamHI | B |
| PstI | Ps |
| SstI | Ss |
| NcoI | |
| HaeII | Ha |
| HindIII | H |
| SspI | |
| SphI | Sp |
| SalI | S |

Used DNA linkers
BglII linkers d(pGGAAGATCTTCC)
EcoRI linkers d(pCCGGAATTCCGG)
SstI linkers d(pCGAGCTCG)

10.A. Construction of pYA235 and its Derivatives The plasmid pYA235 contains a derivative asd$^+$ gene from S. mutans, in that the EcoRI sites have been removed from the native gene.

The BglII to AvaI fragment from pYA631 (Cardineau and Curtiss (1987)), which contains the S. mutans asd$^+$ gene including its promoter sequence, was filled using the Klenow fragment of DNA polymerase I (Klenow), and was cloned into the HincII site of pUC18. This fragment also contains a Tc$^r$ gene. A resultant plasmid is pYA220. The construct with the asd gene in the opposite orientation is unstable.

Much of the Tc$^r$ gene, as well as a number of cleavage sites for restriction enzymes were deleted from pYA220 as follows. The plasmid was digested with SmaI followed by Ba131 digestion, treated with Klenow to fill in overhangs, and ligated. A resultant plasmid was pYA224.

The EcoRI site in the asd gene of pYA224 was removed by partial digestion with EcoRI, followed by treatment with Klenow, and religation. A resulting plasmid, pYA227, does not complement the Asd$^-$ phenotype of delta-asd mutant cells. The treatment causes the insertion of four bases, and results in the conversion of the TGG,AAT,TCA,ATC sequence which encodes Trp,Asn,Ser,Ileur to TGG,AAT, TAA,TTC which encodes Trp,Asn and a translation termination signal.

The asd$^-$ gene of pYA227 was converted to an asd$^+$ gene by intragenic suppression, i.e., a base pair deletion which restores the correct reading frame. pYA227 was transformed into Chi6096 (Table 1), which has a delta-asd mutation. The transformants were grown in the presence of DAP to high density, concentrated in buffered saline containing gelatin, and plated on L agar plates lacking DAP. Colonies which were Asd⁺ occurred at a frequency of $10^{-9}$, however, these colonies also regained the EcoRI site. One colony, which occurred at a frequency of $10^{-10}$, was isolated which was Asd⁺, but which did not regain the EcoRI site. A plasmid isolated from this colony was designated pYA233.

The remaining EcoRI site in pYA233 was eliminated by digestion with EcoRI, followed by treatment with Klenow, and religation. A resulting plasmid, pYA235r lacked EcoRI sites.

The BamHI and/or the PstI sequence in the asd gene of pYA235 may also be eliminated using known techniques.

10.B. Construction of pYA237.

Figure 4:
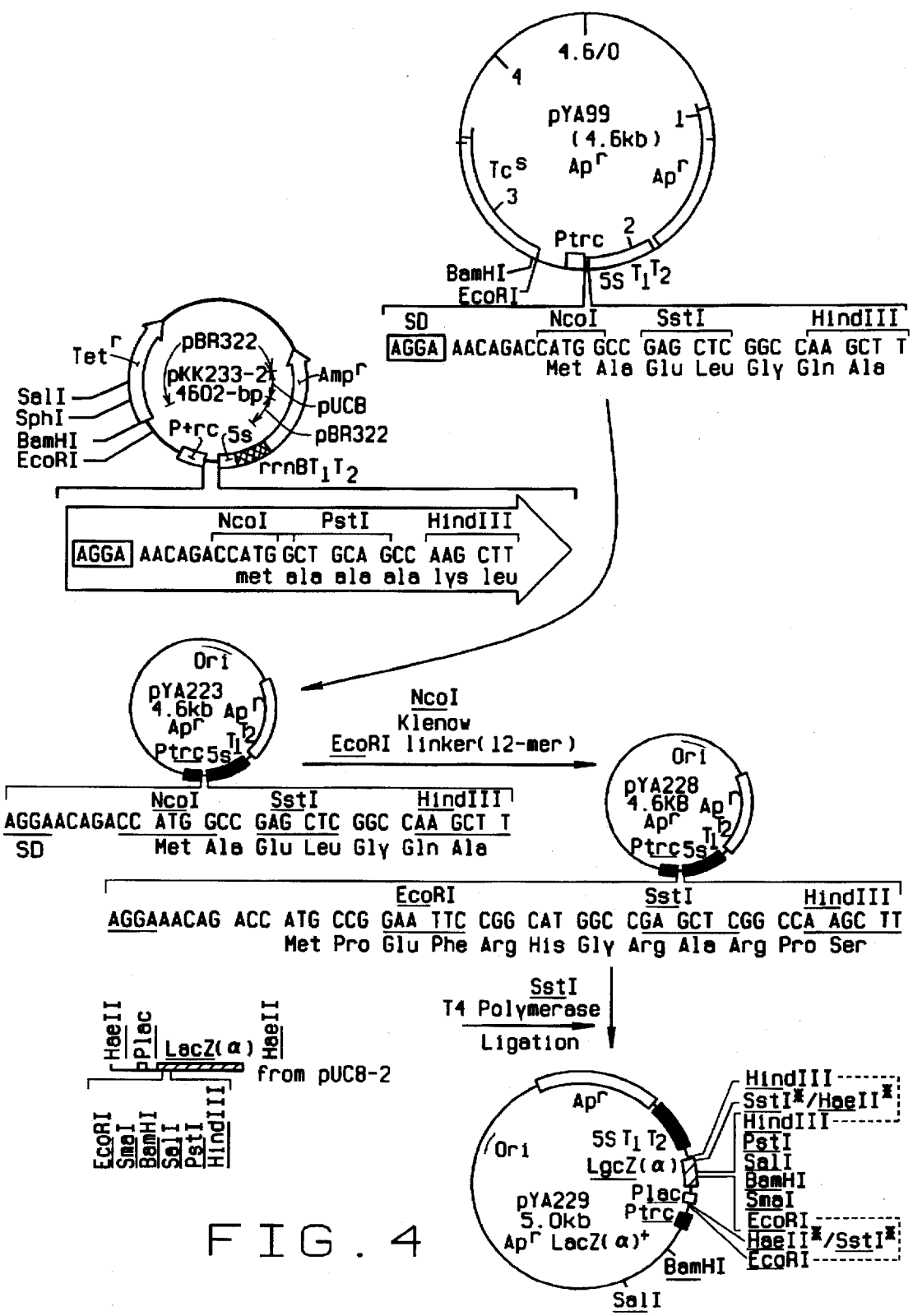
FIG. 4 is a flow chart which shows the significant features of the plasmids used in the construction of pYA229.

The expression vector pYA237, which contains the Ptrc promoter, restriction enzyme sites into which a heterologous gene can be cloned, the S. mutans asd⁺ gene and rrnB termination signals, was constructed as follows (see FIG. 4).

The pKK233-2 plasmid expression vector (Amann and Brosius (1985)) was digested with PstI, treated with T4 DNA polymerase, and SstI linkers (Table 3) were added prior to ligation. A resultant plasmid was isolated, pYA99.

The EcoRI site in pYA99 was replaced by a BglII site. pYA99 was digested with EcoRI, filled with Klenow, and BglII linkers (Table 3) were added prior to ligation. A resultant plasmid was isolated, pYA223.

An EcoRI linker, d(pCCGGAATTCCGG) (Table 3), was inserted into pYA223 at the NcoI site (after filling with Klenow). A resultant plasmid was isolated, pYA228. The EcoRI site in this vector now has the same reading frame specificity as the EcoRI site in lambda-gt11.

A HaeII fragment of pUC8-2 was cloned into the SstI site (treated with T4 DNA polymerase) of pYA228. A plasmid was isolated, pYA229. This plasmid has the lac promoter and the lacZ (alpha) coding sequence.

pYA229 was digested with EcoRI to eliminate the EcoRI fragment containing the lac promoter. A resulting plasmid, pYA230, was transformed into M83 (Table 1). Cells containing pYA230 were light blue on agar with the chromogenic X-gal substrate for beta-galactosidase.

The HindIII fragment containing lacZ (alpha) of pYA230 was replaced by the HindIII fragment specifying the S. mutans asd⁺ gene from pYA235 (Example 10.A.) to yield pYA237.

Other HindIII fragments from derivatives of pYA235, which contain the S. mutans asd gene lacking EcoRt and BamHI sites, and lacking EcoRI, BamHI and PstI sites are also inserted to replace the lacZ (alpha) of pYA230.

Plasmid pYA237 is stably maintained in Chi6097/pYA232 and Chi6060 (see Table 2), but is unstable in Chi6096 and LE392.

10.C. Construction of pYA248

The cloning vector pYA248 allows insertion of cloned DNA fragments using EcoRI, SmaI, SphI, and SalI restriction enzymes. It was constructed as follows.

Figure 5:
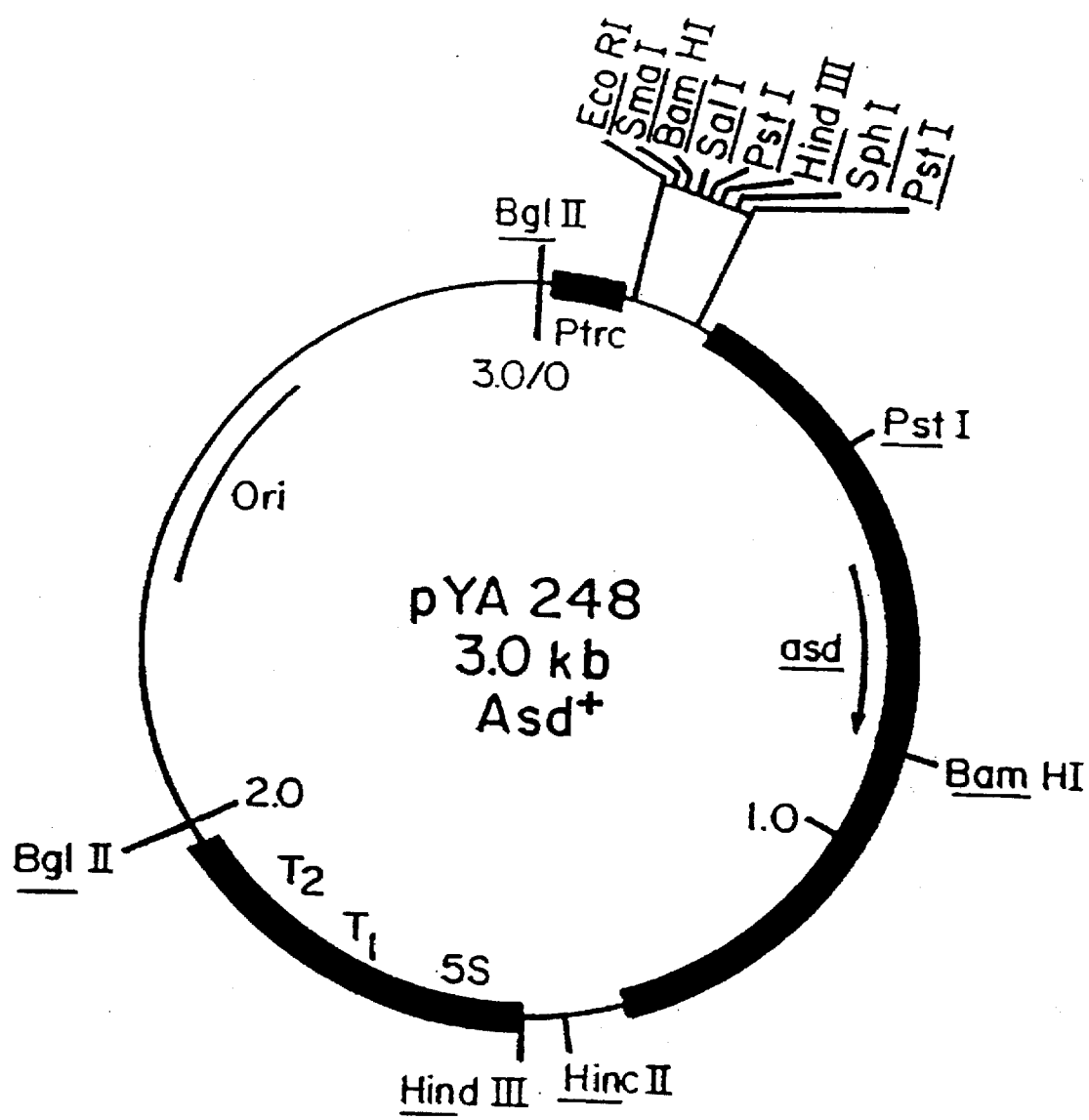
FIG. 5 is a map which shows the significant features of the cloning vector pYA248.

The pISA replicon is wholly contained on a 1.0 kb HincII fragment. This fragment was ligated with the SspI fragment from pYA237 (FIG. 4), which contains the Ptrc MCS asd⁺ rrnB sequence, by using BglII linkers. The resulting plasmid is the 3.0 kb cloning vector pYA248. Important features of the vector are shown in FIG. 5.

Analogous cloning vectors to pYA248 are constructed by the removal of the BamHI and PstI sites within the asd gene (See Example 10.A.). Removal of these sites allows the use of these enzymes for cloning.

The nucleotide sequence of the Ptrc promoter and the multiple cloning sites in pYA248 are given in FIG. 6.

11. Construction of an Expression Vector containing an asd⁺ Gene, and a Gene Encoding Beta-galactosidase.

Figure 7:
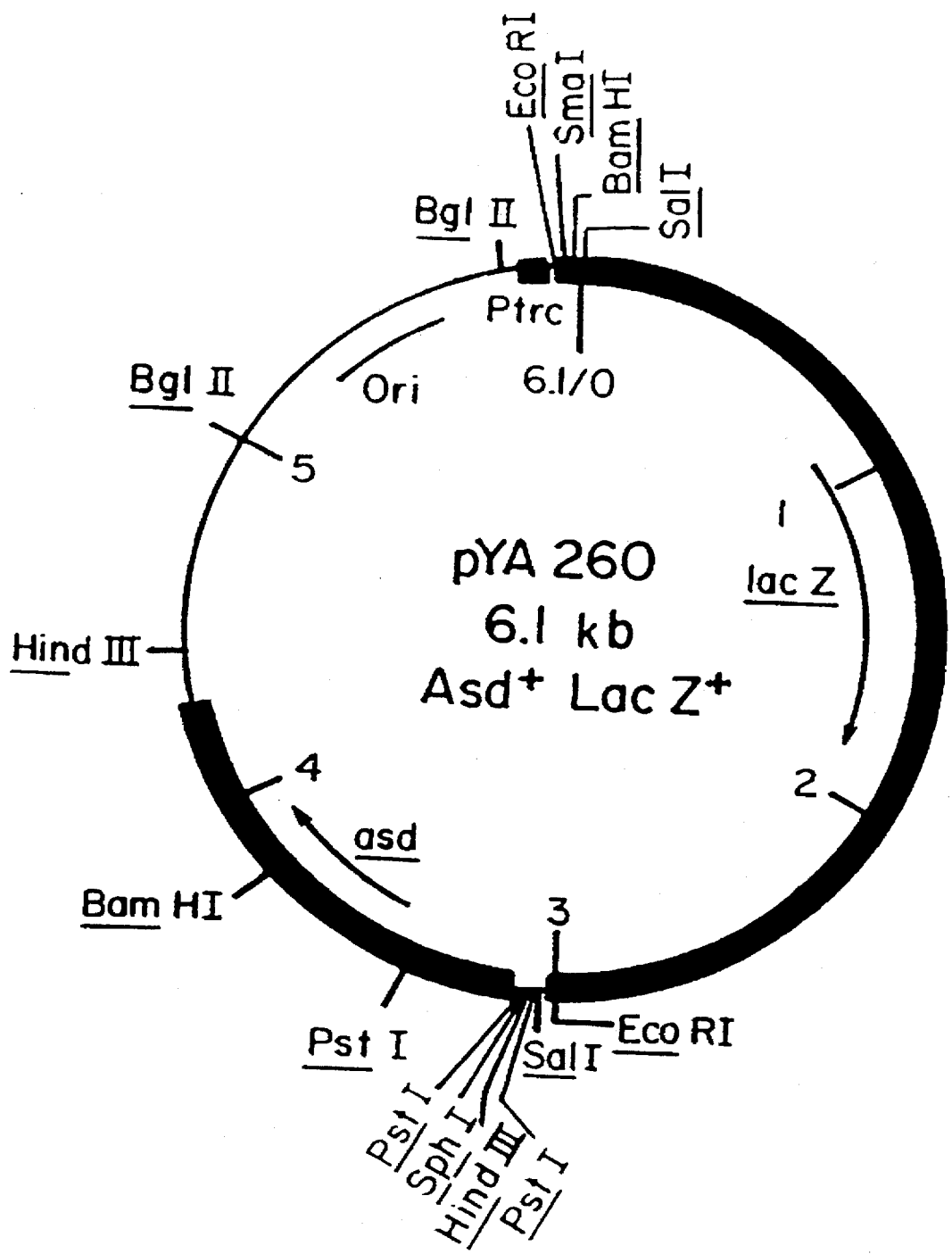
FIG. 7 is a map which shows the significant features of the recombinant vector pYA260.

The SalI fragment (3.1 kb) from pSGMU37, which contains lacZ was inserted into the SalI site of pYA248. The resulting plasmid is pYA260. Significant features of pYA260 are shown in FIG. 7.

12. Expression of the Genes Encoding Beta-Galactosidase and ASD in asd⁻ Mutants of S. typhimurium and E. coli.

Figure 8:
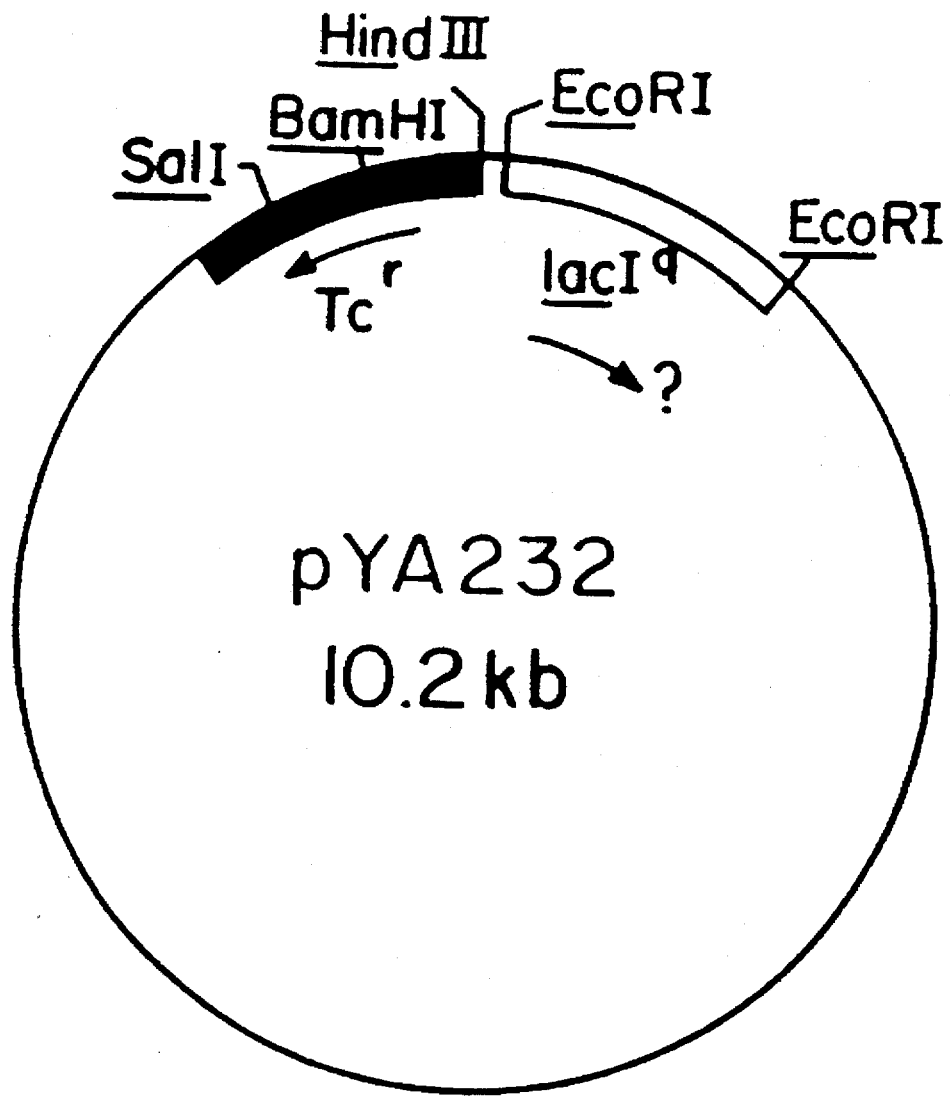
FIG. 8 is a map which shows the significant features of pYA232.

The Asd⁻ strains Chi3115, Chi4072, and Chi2984 are transformed with pYA260 or pYA248, and grown in medium without DAP under conditions which allow protein synthesis. In addition, Chi2984 is cotransformed with pYA260 and pYA232. Significant features of pYA232 are shown in FIG. 8; this plasmid specifies the lacI$^q$ repressor.

Figure 9:
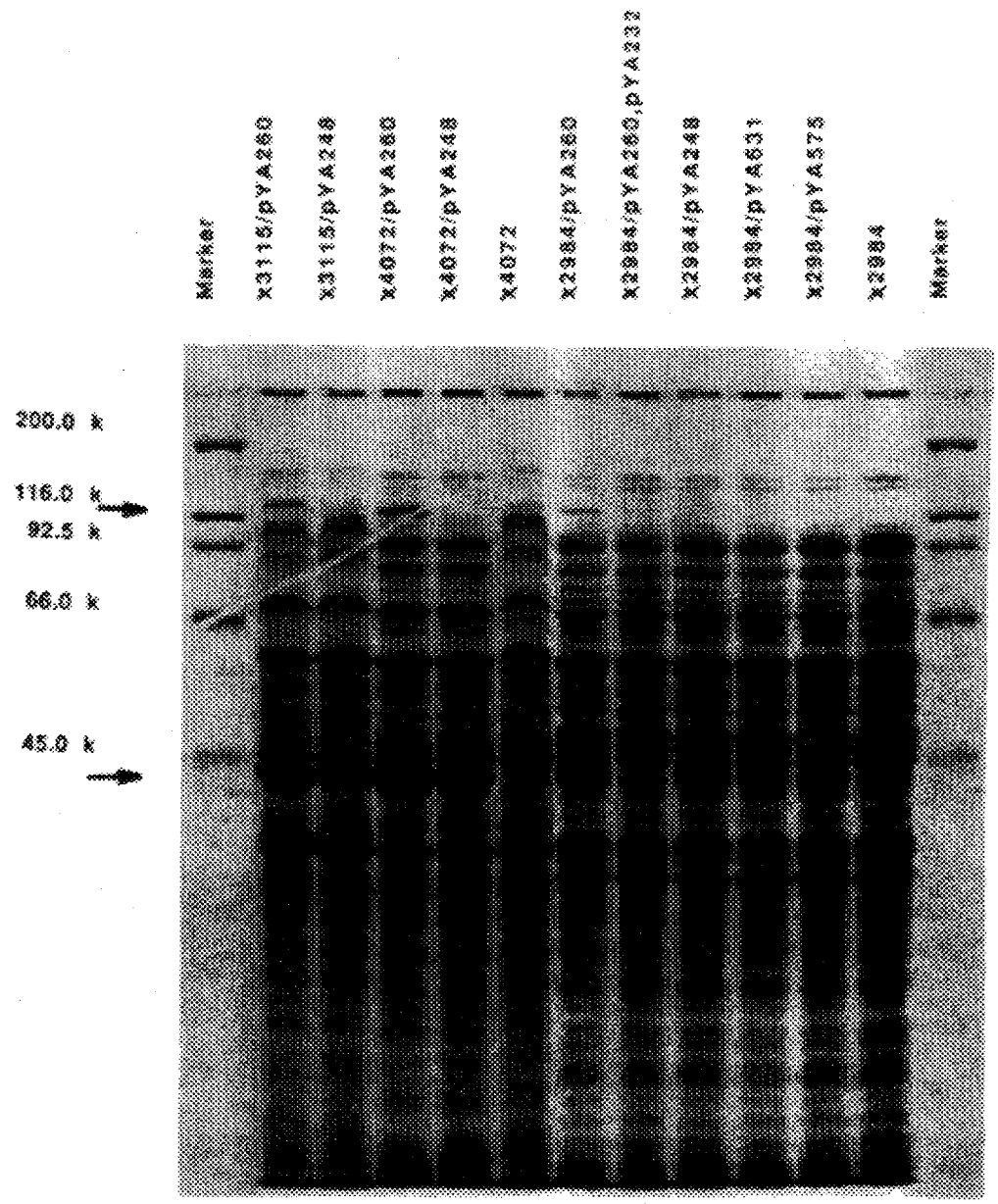
FIG. 9 is a photo of a polyacrylamide gel which shows the expression products of Asd⁻ strains transformed with pYA260 or pYA248, or cotransformed with pYA260 and pYA232.

The products synthesized by the transformed cells, and by control cells, are analyzed by electrophoresis on SDS-polyacrylamide gels as described by Laemmli (see Methods in Enzymology). A photograph of a gel containing the separated products is shown in FIG. 9.

Chi3115, Chi4072, and Chi2984 transformed with pYA260 synthesize both Asd protein and beta-galactosidase. However, Chi2984 cotransformed with both pYA260 and pYA232 does not synthesize b-galactosidase due to the lacI$^q$ repressor specified by pYA232. The Asd protein is made in great abundance by all delta-asd strains which are transformed with either pYA248 or pYA260.

13. Construction of an Expression Vector Containing an asd gene and a spaA gene.

Figure 10:
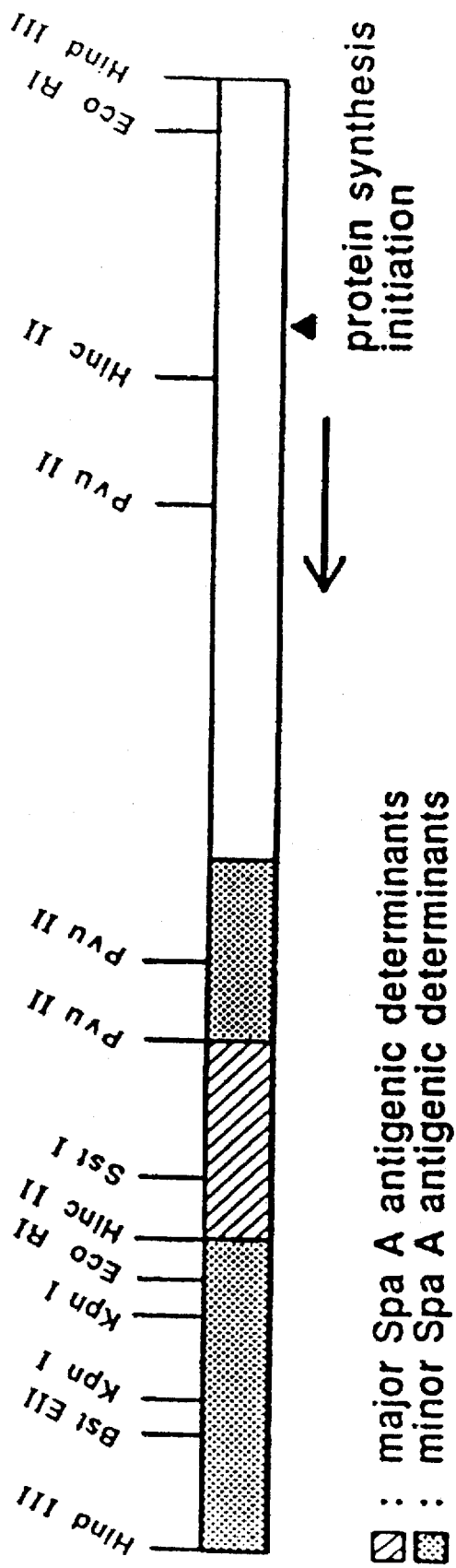
FIG. 10 is a map which shows the structure of *S. mutans* spaA gene indicating major antigenic determinants.

The structure of the S. mutans spaA gene indicating major antigenic determinants is shown in FIG. 10.

Figure 11:
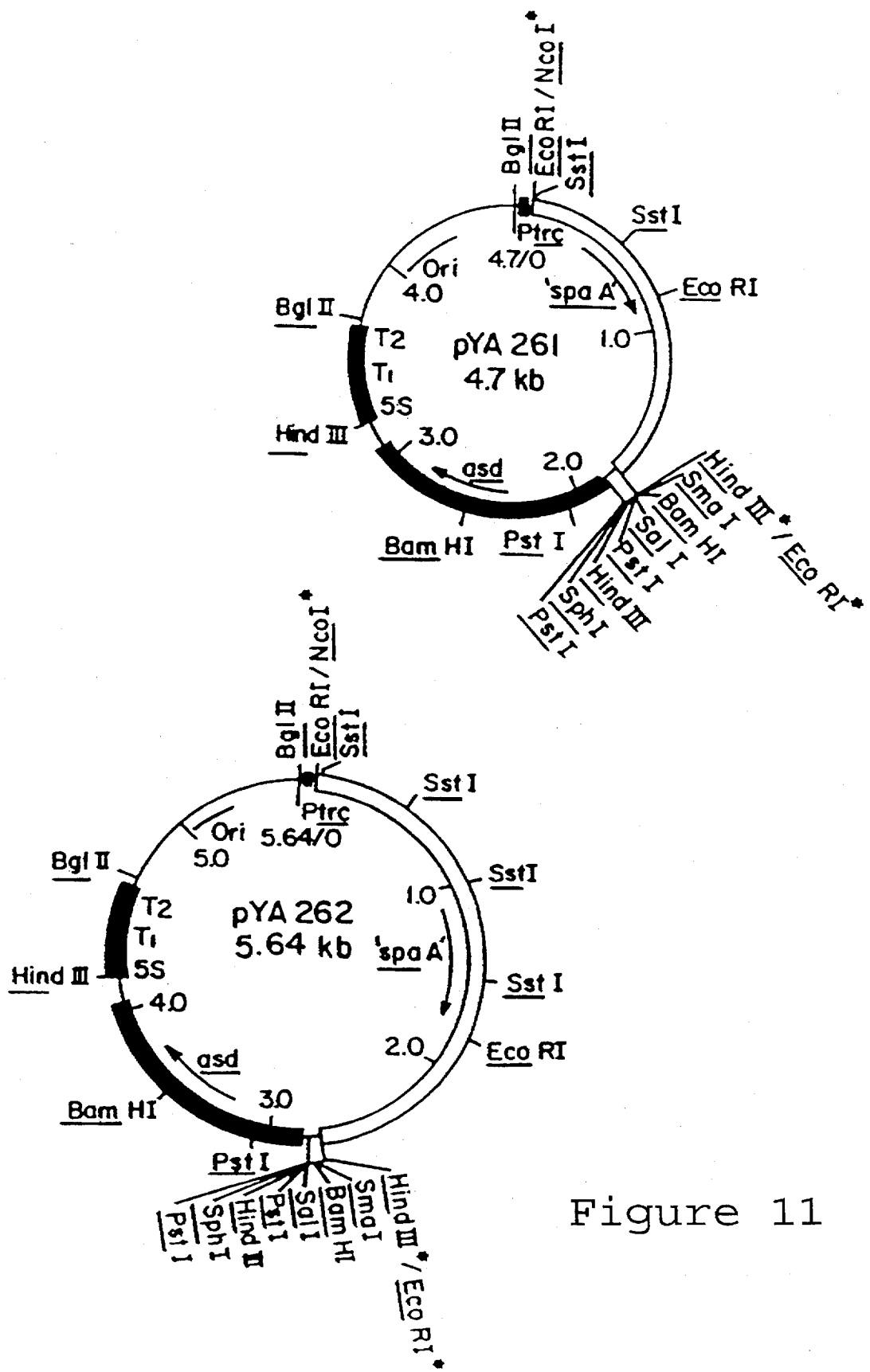
FIG. 11 are maps which show the significant features of pYA261 and pYA262.

The DNA of pYA248 is linearized by treatment with EcoRI. The ends of the DNA are treated with Klenow and bacterial alkaline phosphatase. The NcoI-HindIII fragment of pYA177, which contains the spaA gene is treated with Klenow. The two DNAs are ligated with $T_4$ DNA ligase to yield pYa261. Since the major antigenic determinant of the SpaA protein is mainly located in the SstI fragment (See FIG. 10), the SstI fragment of pYa261 was purified and ligated with the rest of pYA261 to make tandem repeats of that region, maintaining the reading frame of the spaA gene. Plasmid pYA262 containing three tandem repeats of the SstI fragment was obtained. pYA261 and pYA262 are depicted in FIG. 11.

14. In Vitro Stability of pYA260, pYA261 and pYA262 in Chi4072.

Figure 12:
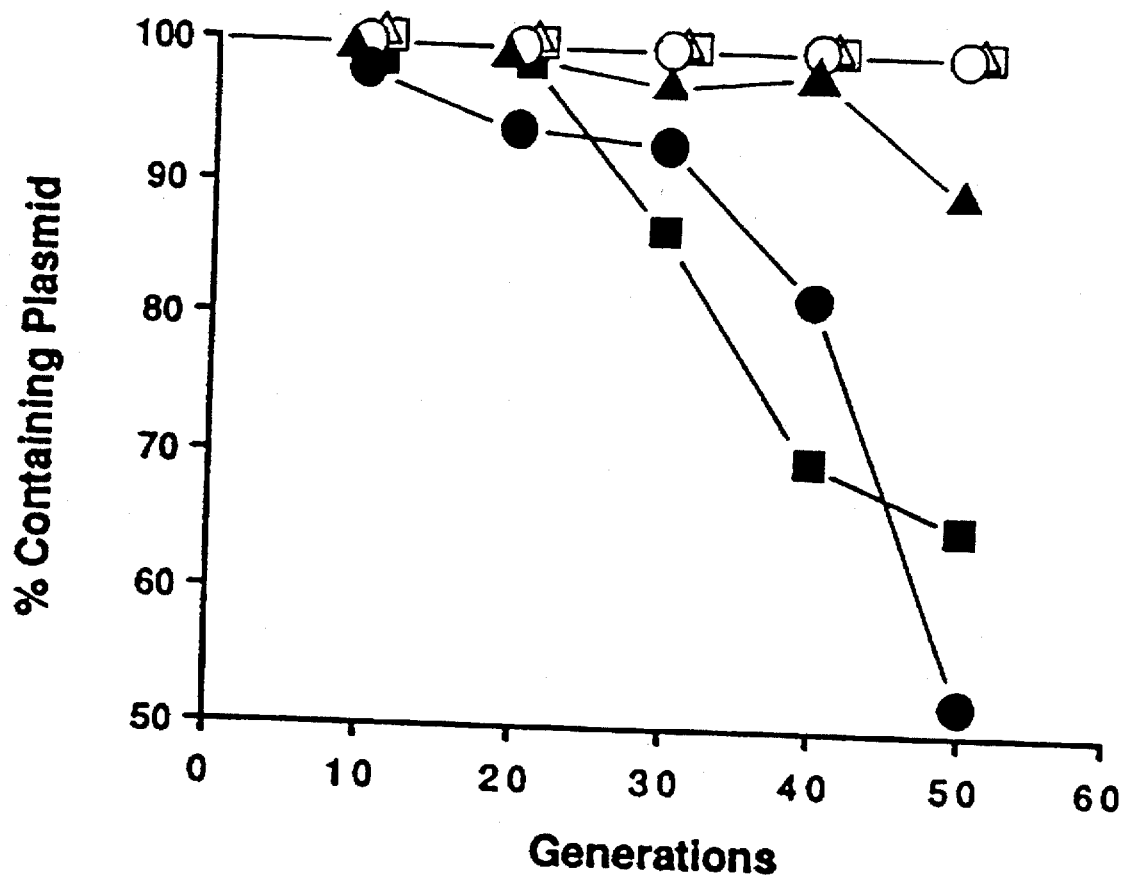
FIG. 12 is a graph which shows the spontaneous rates of loss of pYA260, pYA261, and pYA262 from an Asd⁻ strain.

The in vitro stability of pYA260 (open circles, closed circles) pYA 261 (open triangles, closed triangles), and pYA 262 (open squares, closed squares) in Chi4072 is determined by incubating the cells in L-broth in the presence (closed symbols) or absence (open symbols) of DAP, and monitoring the percentage of cells that are Asd⁺ LacZ⁺ and Spa⁺ in the descendant generations. As shown by the results in FIG. 12, the spontaneous rate of pYA260 loss is 1%/bacterium/generation, with the smaller plasmids, pYA261 and pYA262, being more stable.

15. Expression of SpaA Antigen from pYA261 and pYA262.

Figure 13:
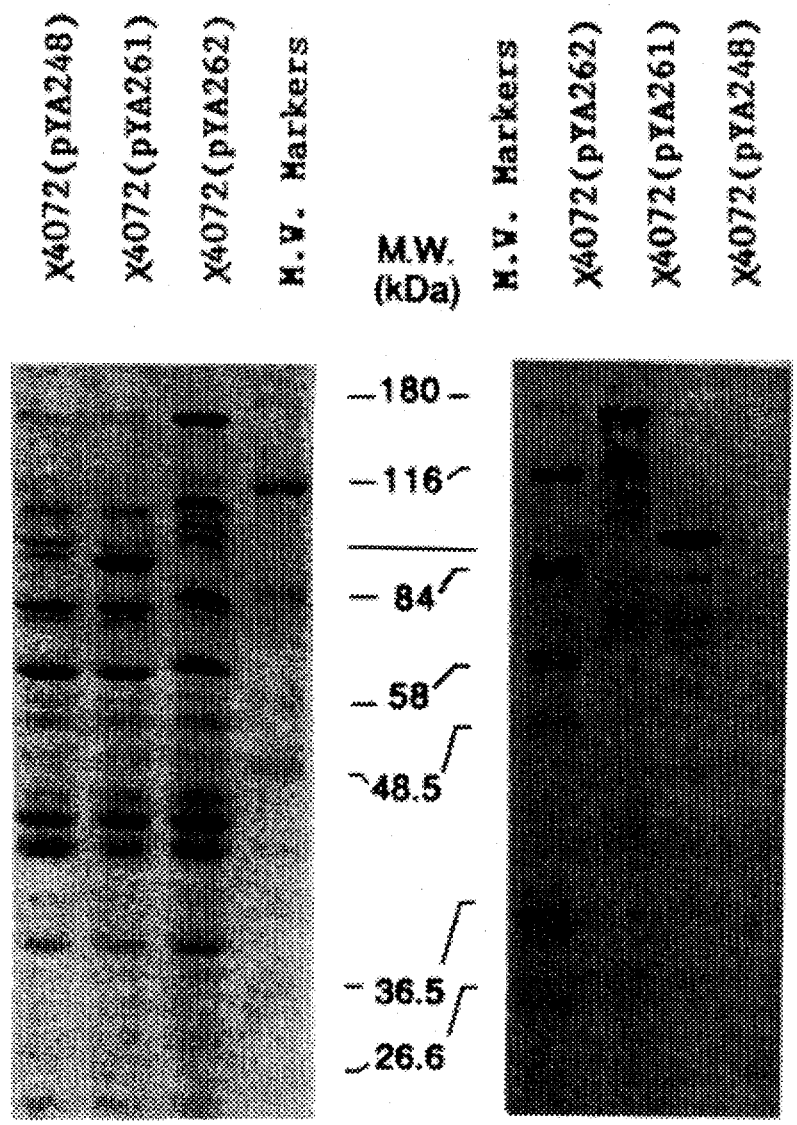
FIG. 13 is a photo of a gel which shows the Coomassie blue-stained SDS-PAGE profiles (left) and Western blots (right) of whole cell proteins of *S. typhimurium* Chi4072 containing Asd⁺ plasmids pYA248, pYA261, and pYA262.

Chi4072 is an avirulent derivative of S. typhimurium that is highly immunogenic when orally fed to mice (see Curtiss and Kelly, (1987) and Nakayama et al, (1988)). pYA 261 and pYA262 are transformed into Chi4072. The production of SpaA protein is evident both by Coomassie blue staining of SDS polyacrylamide gel electrophoresis profiles and by Western blot analysis using anti-SpaA sera (See FIG. 13). It is evident that the delta-cya delta-crp strains produce the SpaA protein to a very substantial extent and this exceeds the production of SpaA protein by recombinant strains of E. coli K-12 and by other avirulent Salmonella vaccine strains.

The SpaA protein is the principal surface protein on the S. mutans cell surface and is necessary for S. mutans to attach to salivary proteins on the tooth surface Curtiss, 1985, Current Topics in Microbiology and Immunology 118:253–277. SpaA-deficient mutants of S. mutans are unable to colonize germ-free rats and thus are unable to induce dental caries. Thus delivery of the SpaA antigen to the GALT stimulates a mucosal immune response which should prevent S. mutans colonization.

Ultimately mice immunized with Chi4072 containing pYA262 can be placed on a sucrose-containing diet and then challenged with a virulent S. mutans strain (UAB66). Ability of UAB66 to colonize in teeth is investigated first and then effectiveness to prevent caries. Colonization is evaluated during the first week or two after challenge whereas caries prevention is scored six to twelve weeks after challenge.

16. In vivo stability of pYA262 in Chi4072.

Chi 4072 cells containing pYA262 were orally fed to Balb c mice. These cells attach to, invade, and persist in the Galt. As indicated by the data in Table 4, 100 percent of Chi4072 isolates obtained up to three weeks after initial inoculation of mice were $Asd^+$ and continued to produce the SpaA protein. This justifies the assertion that the use of an $Asd^+$ vector in an avirulent strain such as Chi4072 with a delta-asd mutation will lead to stable maintenance of the recombinant gene in an environment with no exogenous selective pressure. Mice so immunized with Chi4072 cells harboring pYA262 develop secretory IgA in saliva and serum IgG against SpaA protein as well as display a delated type hypersensitivity (DTH) reaction to SpaA protein injected into the hind footpad. The small fraction of the Chi4072 cells harboring pYA261 or pYA262 that lose the plasmid each generation undergo DAPless death, to liberate their cellular contents to enhance immunization of the animal host. This is a preferred attribute of the invention.

TABLE 4

In vivo stability of pYA262 specifying SpaA protein in S. typhimurium SR-11 Δcya Δcrp Δasd strain X4072[a]

| Day sacrificed | Mouse | Total cfu in Peyer's patches | pYA262[b] Asd+ | pYA262[b] SpaA+ | Total cfu in spleen | pYA262[b] Asd+ | pYA262[b] SpaA+ |
|---|---|---|---|---|---|---|---|
| 1 | 1 | $2 \times 10^2$ | 12/12 | 12/12 | N/T | N/T | N/T |
|   | 2 | $6 \times 10^1$ | 4/4 | 4/4 | N/T | N/T | N/T |
|   | 3 | $1 \times 10^2$ | 7/7 | 7/7 | N/T | N/T | N/T |
| 4 | 1 | $1 \times 10^4$ | 20/20 | 20/20 | $2 \times 10^2$ | 13/13 | 13/13 |
|   | 2 | $2 \times 10^4$ | 20/20 | 20/20 | <10 | N/A | N/A |
|   | 3 | $5 \times 10^3$ | 20/20 | 20/20 | <10 | N/A | N/A |
| 7 | 1 | $2 \times 10^5$ | 20/20 | 20/20 | $1 \times 10^3$ | 20/20 | 20/20 |
|   | 2 | $1 \times 10^5$ | 20/20 | 20/20 | $5 \times 10^1$ | 3/3 | 3/3 |
|   | 3 | $1 \times 10^5$ | 20/20 | 20/20 | <10 | N/A | N/A |
| 14 | 1 | $7 \times 10^3$ | 20/20 | 20/20 | $1 \times 10^2$ | 11/11 | 11/11 |
|   | 2 | $5 \times 10^3$ | 20/20 | 20/20 | $8 \times 10^1$ | 5/5 | 5/5 |
|   | 3 | <10 | N/A | N/A | $5 \times 10^2$ | 20/20 | 20/20 |
| 21 | 1 | $1.6 \times 10^3$ | 20/20 | 20/20 | $2.4 \times 10^2$ | 16/16 | 16/16 |
|   | 2 | $9.9 \times 10^2$ | 20/20 | 20/20 | $1.5 \times 10^1$ | 1/1 | 1/1 |
|   | 3 | $5.7 \times 10^2$ | 20/20 | 20/20 | <10 | N/A | N/A |

[a]Eight-week-old BALB/c mice were orally inoculated with $1.2 \times 10^9$ X4072 (pYA262) cells on Day 0.
[b]Number positive/number tested. N/T = not tested. N/A = none available for testing.

17. Cloning of S. typhimurium $asd^+$ Gene and Construction of pYA272, pYA275, and pYA277.

DNA libraries of S. typhimurium SR11 (Chi3306) DNA wee constructed using various restriction enzymes to digest the DNA and cloning vectors. The S. typhimurium $asd^+$ gene was initially identified in several cosmid libraries and digestion of one of these recombinants with PstI cloning in pUC18 and selection for $Asd^+$ transformants in Chi6097 yielded pYA272. Subcloning with EcoRI was carried out to yield pYA275 (FIG. 14). Tn1000 mutagenesis led to many insertions in pYA275 and these were transferred to Chi3630 to screen for insertional inactivation of the asd gene. The mutagenesis and screening were essentially as described in Guyer (1983). Based on these results a 1.75 kb EcoRI to SstI fragment containing the S. typhimurium $asd^+$ gene was subcloned into pUC18 to yield pYA277 (FIG. 14).

18. Construction of pYA280.

In order to facilitate the construction of cloning vectors with the S. typhimurium $asd^+$ gene, the vector pYA280 (FIG. 15) was constructed. This vector contains the S. typhimurium $asd^+$ gene in a cassette. pYA 280 was constructed by removing the 1.75 kb EcoRI to PstI fragment containing the S. typhimurium $asd^+$ gene from pYA277, purifying it, removing the 5' overhang at the SstI site, filling in the 3' overhang at the EcoRI site, and then adding BglII linkers by blunt end ligation. The resulting DNA fragment was cloned into a derivative of pUC-4k, in which the PstI site had been converted to a BglII site. The resulting recombinant vector is pYA280, which was introduced into Chi6097.

The S. typhimurium $asd^+$ gene can be removed from pYA280 as a cassette by using the restriction enzymes EcoRI, BamHI, SalI or BglII.

19. Construction of pYA292

Figure 15:
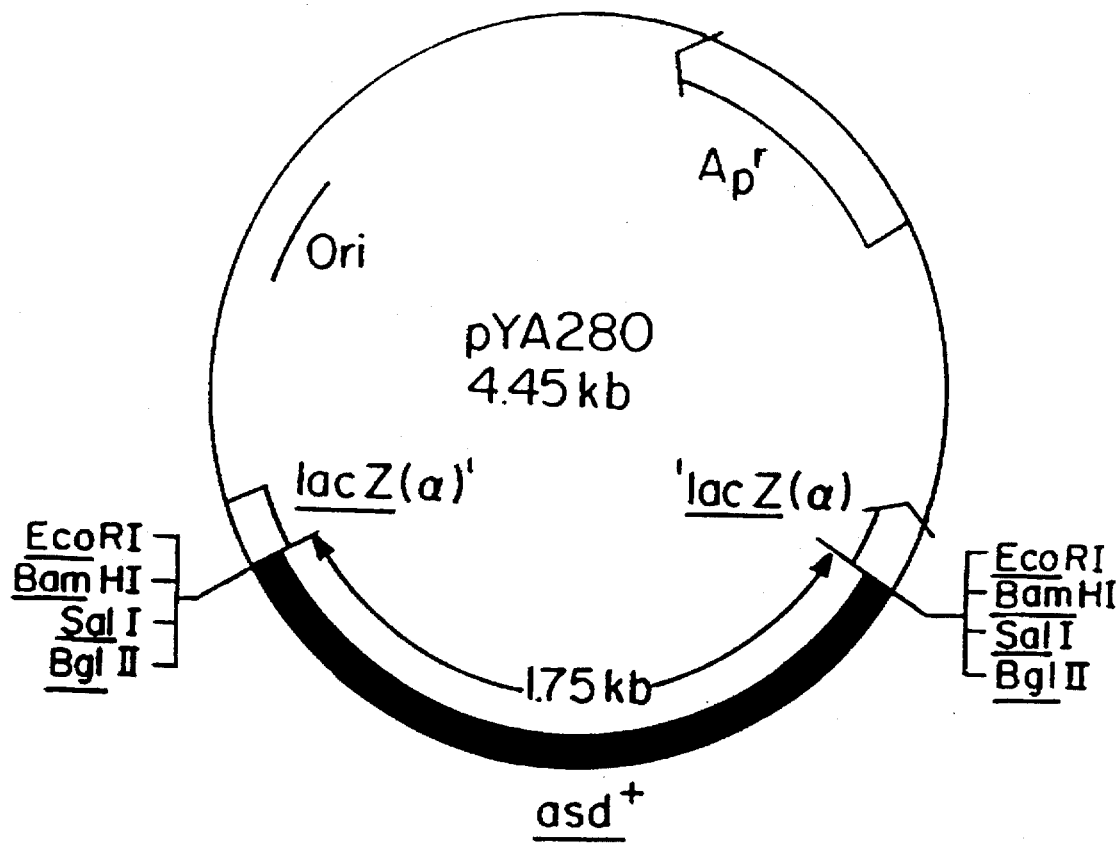
FIG. 15 is a map showing the significant features of pYA280.
Figure 16:
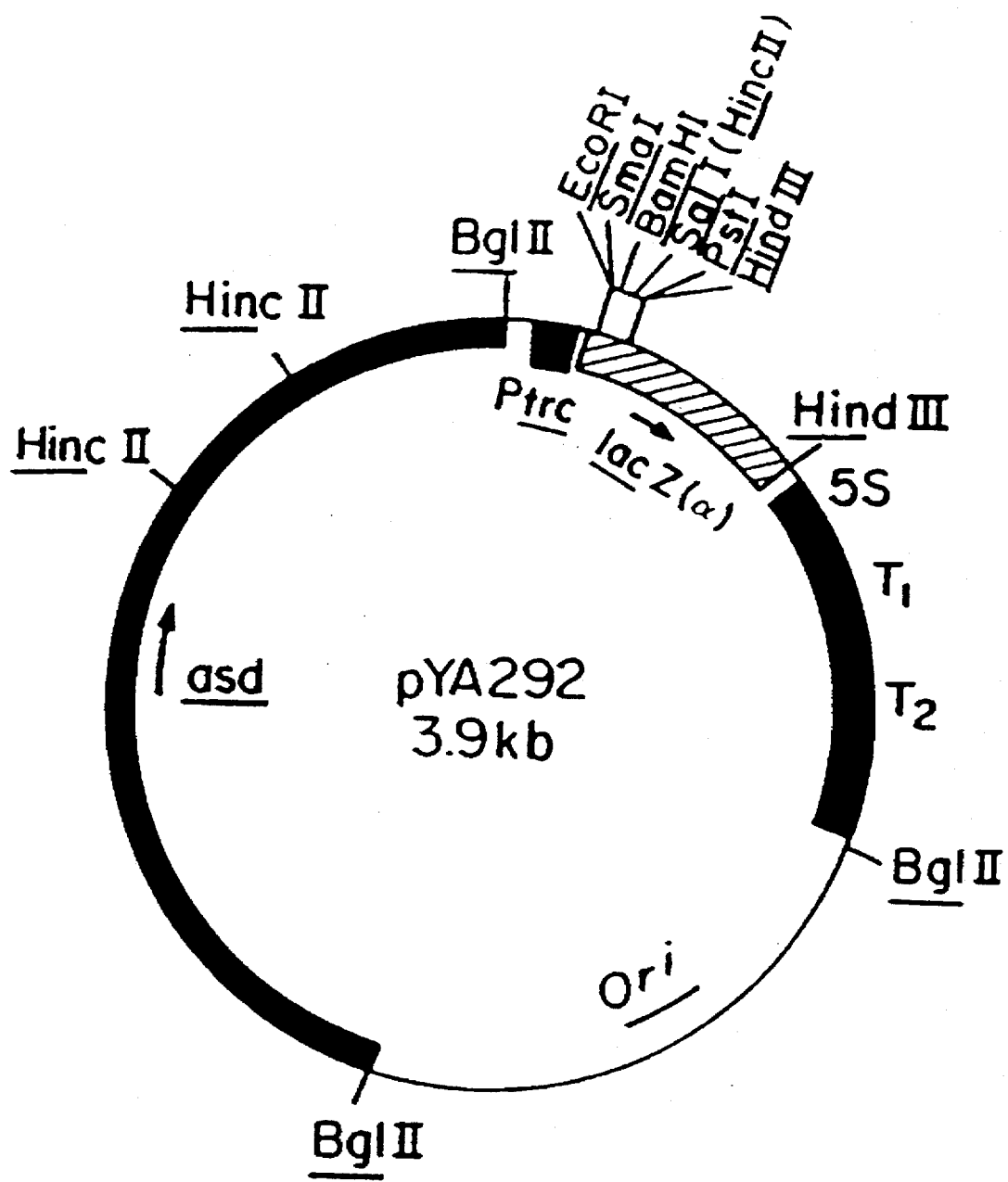
FIG. 16 is a map showing the significant features of pYA292.
Figure 17:
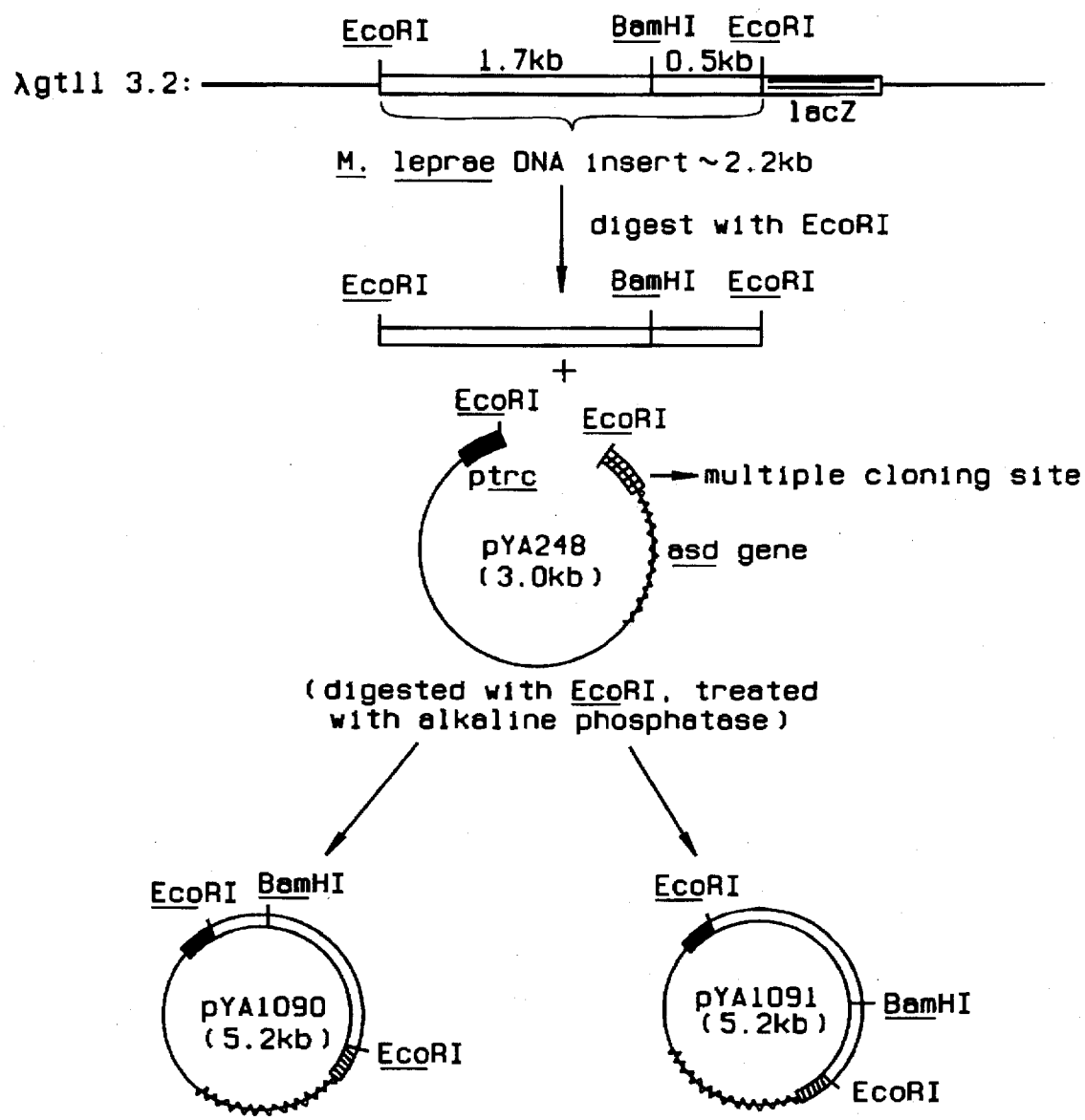
FIG. 17 is a flow chart for the construction of pYA1090 and pYA1091 which contain *M. leprae* DNA insert 3.2.
Figure 18:
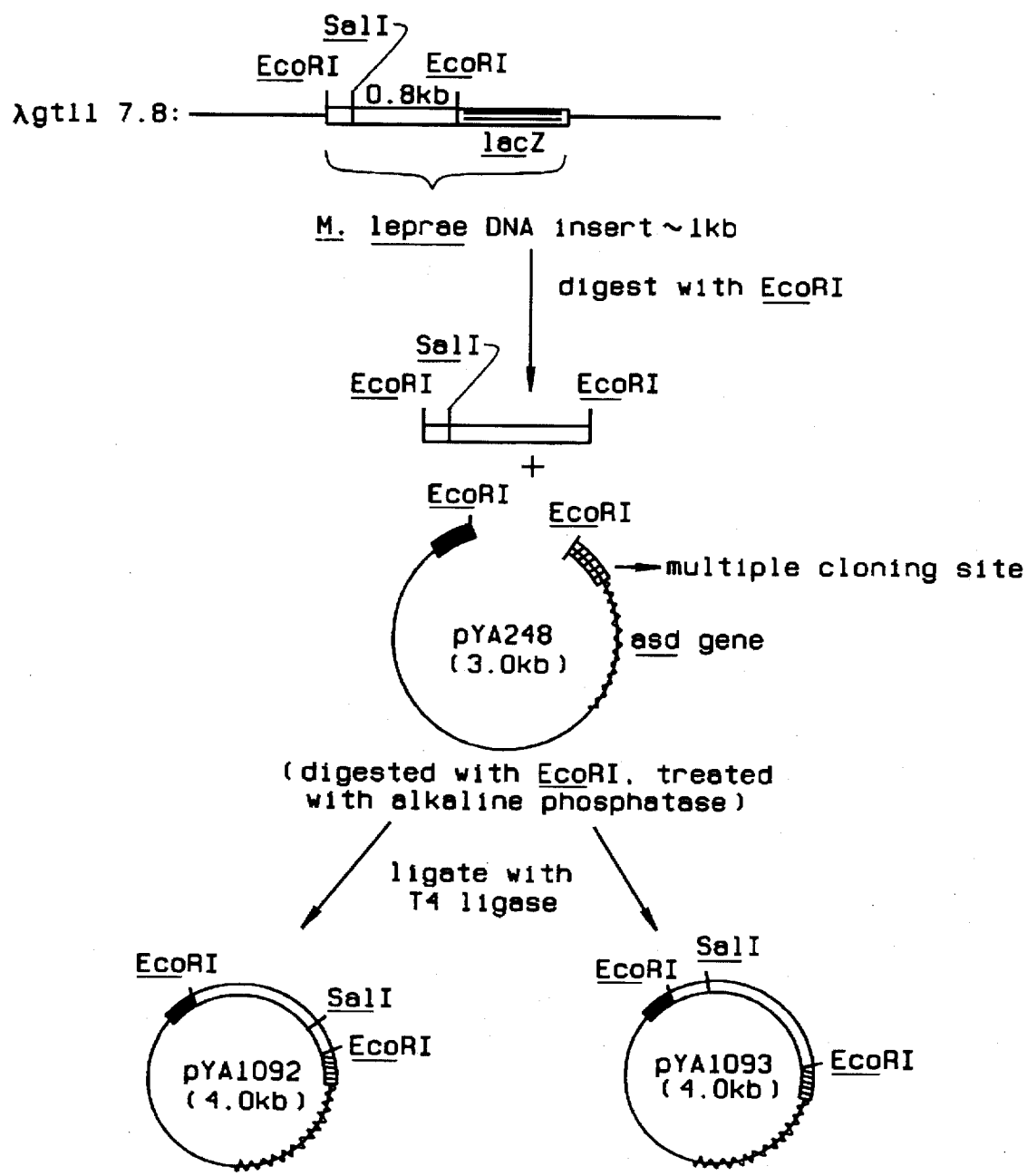
FIG. 18 is a flow chart for the construction of pYA1092 and pYA1093 which contain *M. leprae* DNA insert 7.8.

The cloning vector pYA292 (FIG. 16), was constructed in a number of steps employing standard DNA cloning techniques. pYA292 contains the rrnB transcription terminator and p15A origin of replication from pYA248 (see FIG. 5) as well as the Ptrc promoter up to the HindIII site (see FIG. 6). The 1.75 kb BglII fragment containing the S. typhimurium $asd^+$ gene was derived from pYA280 (FIG. 15). A HindIII fragment containing the lacZ alpha-coding sequencer which was derived from pYA230 (see FIG. 4), was added to allow selection by the appearance of a blue color when Chi6097 containing pYA292 is plated onto a medium containing the chromogenic substrate X-gal. The insertion of DNA fragments into any one of the potential cloning sites in pYA292 usually results in a loss of the ability to hydrolyze beta-galactosides, yielding white colonies under these plating conditions. However, this loss of ability to hydrolyze beta-galactosides may not occur if the insertion is such that it allows the synthesis of an enzymatically active beta-galactosidase fusion protein. The cloning sites in pYA292 include the restriction enzyme sites for EcoRI, SmaI, BamHI, SalI, and PstI.

20. Construction of Expression Vectors Containing an $asd^+$ Gene, and a Gene Encoding M. leprae antigens 20.A. Isolation of Clones encoding M. leprae antigens from a lambda-gt11 library A library of M. Leprae antigens in lambda-gt11 is prepared by randomly shearing M. Leprae DNA and cloning the DNA into the EcoRI site of the vector so that mycobacterial polypeptides are produced as a fusion protein with beta-galactosidase. The expression of the beta-galactosidase library is under the control of the lac operon such that they can be induced by isopropyl beta-D-thiogalactopyranoside (IPTG).

The lambda-gt11::M. leprae library is plaqued on E. coli Y1090 to yield approximately 5000 plaques per plate, and the plates are incubated at 42° C. for 2 hrs to induce the bacteriophages. The plaques are then overlaid with nitrocellulose membranes that are soaked in 10 mM IPTG and incubated for a further 2 hr at 37° C. The nitro-cellulose membranes are washed in Tris buffer pH 8.0 containing 0.5% Tween 80 and are blocked with 0.25% BSA+0.25% gelatin in the same buffer. The sera from lepromatous patients used was a gift from Dr. Thomas H. Rae. The sera from 21 patients is pooled and extensively absorbed with whole cells and sonic extracts from *E. coli* Y1090. Sonic extracts are coupled to cyanogen bromide activated Sepharose 4B as well as spotted onto nitrocellulose membranes and is used to remove cross-reactive antibodies. The nitrocellulose filters containing the plaques are incubated at a 1:1000 dilution of the LL sera, washed and then incubated with anti-human antibodies conjugated to alkaline phosphatase and the reactivity is assessed by using the chromogenic substrate mixture of Nitro Blue Tetrazolium (NBT) and Bromochloro indolyl phosphate (BCIP). Plaques producing positive signals are purified by reisolating three times in a similar manner. Using this methodology, a total of 20 recombinant clones are identified. Different clones show different reactivity in the intensity of reactivity to LL sera.

The library is screened for expression product reactivity with the following: a monoclonal antibody against a *M. leprae* 65kDa protein (Buchanan et al (1987)); sera from patients with lepromatous form of the disease (LL), and with the tubercular form of the disease (TT). Products are also identified by Western blot analysis.

The immunological reactivity of two clones, 3-2 and 7-8, is shown in Table 5.

TABLE 5

| | Characteristics of lamboda gt11::*M. leprae* immunologically reactive Clones | | | | |
|---|---|---|---|---|---|
| Clone No. | Insert Size (kb) | Reactivity LL sera | Reactivity TT sera | Reactivity Mab | M.W. |
| 3-2 | 2.2 | ++++ | + | anti 65kDa | 132 |
| 7-8 | 1.0 | +++ | + | — | 158/153 |

— = no reactivity;
+ to ++++ = subjective visual grading;
Mab = monoclonal antibody.

20.B. Construction of Expression Vectors Containing Genes Encoding asd and *M. leprae* antigens.

Purified EcoRI inserts from the lambda-gt11 clones 3-2 and 7-8, described in Example 20.A., are inserted into pYA248 as indicated by the flow charts in FIG. 17 and FIG. 18. The resulting recombinant vectors are pYA1090 and pYA1091 containing the insert from clone 3-2, and pYA1092 and pYA1093 containing the insert from clone 7-8. Characteristics of these vectors and their *M. leprae* expression products are given in Table 6. pYA1090 and pYA1092 have the correct orientation with respect to the Ptrc promoter and express polypeptides that react with patient sera.

TABLE 6

| Characterization of Subclones | | | |
|---|---|---|---|
| Recombinant molecule | Source of insert | Orientation relative to trc promoter | M.W. of polypeptide |
| pYA1090 | lambda gtll 3.2 | correct | 29*, 27* |
| pYA1091 | lambda gt11 3.2 | reverse | 55, 21 |
| pYA1092 | lambda gt11 7.8 | correct | 36*, 33* |
| pYA1093 | lambda gt11 7.8 | reverse | — |

*React with antibodies in LL patient sera.

21. Effectiveness of a Vaccine Strains Containing pYA1090 and pYA1092.

Vaccine strains are constructed by transforming an avirulent *S. typhimurium* strain Chi4072 (Table 1), which is a deletion mutant lacking adenylate cyclase and cyclic AMP receptor protein, and which also contains a deletion mutation in asd, with pYA1090 and pYA1092.

*M. leprae* replicates slowly in hind footpads of mice. The immune response to vaccines against the microorganism can be monitored either by measuring inability of *M. leprae* to replicate in footpad following immunization or by evidence of delayed-type hypersensitivity (DTH) following injection of killed *M. leprae* extracts into hind footpads of immunized mice. Shepard et al (1980).

Mice are immunized with $10^9$ transformants given orally as described above—i.e., for Chi4072 with pYA261 and pYA262 expressing the *S. mutans* SpA protein. IgA in saliva and IgG in serum against the *M. leprae* antigen is quantitated weekly following immunization. One month following immunization some mice are injected in one of their two hind footpads with suitable quantities of a killed *M. leprae* extract. Buffered saline is injected into the other footpad as a control. A cellular immune response is detected by a DTH reaction which is manifested by swelling of the footpad injected with the *M. leprae* extract. Another group of immunized mice are inoculated with $10^4$ viable *M. leprae* cells in one hind footpad. Six to nine months later the titer of *M. leprae* cells is determined either by microscopic examination of by use of a *M. leprae* specific DNA probe. A mouse with no effective immunity should display about $10^6$ *M. leprae* cells (a 100-fold increase in the inoculum). A mouse with effective immunity will have $10^4$ cells or even lower numbers if the *M. leprae* have been killed and destroyed by macrophages.

This procedure can be repeated with numerous Chi4072 derivatives expressing different *M. leprae* antigens identified by reactivity with antibodies in sera from LL and TT patients. Ultimately the best antigen candidates can be selected and evaluated in armadillos and then in humans as an anti-leprosy vaccine.

18. Removal of gyrA1816 Allele Conferring Nalidixic Acid Resistance in Vaccine Strains.

The EPA, USDA, and FDA do not permit genes for antibiotic resistance in strains to be used as live vaccines. The gyrA1816 mutation was introduced into many avirulent *S. typhimurium* mutants as a means to readily follow and quantitate the survival of such strains in laboratory experiments employing mice. Prior to use of such strains as licensable vaccines, it is essential to remove the 9yrA1816 mutation. This can be done by making use of strain DB9031 (Table 1) which has zeh-4::Tn10 which is 95% linked by cotransduction with the $9/rA^+$ gene.

Propagate p22HTint on DB9031 to make a transducing lysate by the methods described above. After removal of bacterial debris, the lysate is stored over chloroform at 4° C. The P22HTint lysate propagated on DB9031 can be used to infect a strain with a gyrA1816 allele such as Chi4072 (Table 1) using a multiplicity of infection of approximately 0.3. The Chi4072 will, of course, require growth in Luria broth supplemented with diaminopimelic acid.

Following 20 minutes for adsorption and injection, suitable dilutions are plated on Penassay agar containing DAP and 12.5 micrograms per ml of tetracycline. Incubate these plates overnight.

Pick and purify 10 tetracycline-resistant transductants and test to see which have become sensitive to nalidixic acid (5 micrograms per ml) and also retain all other phenotype properties associated with other mutations present in the vaccine strain.

Take a tetracycline-resistant nalidixic acid-sensitive isolate and transduce with P22HTint propagated on strain Chi3000. After allowing several generations to permit cells to become homogeneous with regard to genotype and expression of phenotype, cells are plated on a nutrient agar containing 6 micrograms of fusaric acid per ml and chlorotetracycline (autoclaved) plus any additional required supplements such as DAP. After overnight incubation at 37° C., isolated colonies would be picked, purified, and tested for loss of tetracycline resistance as described above. High concentrations of bacteria would be evaluated for inability to mutate to tetracycline resistance as additional evidence for the absence of vestiges of Tn10.

While the present invention has been illustrated above by certain specific embodiments, it is not intended that these specific examples limit the scope of the invention as described in the appended claims.

Industrial Applicability

Effective immunity with recombinant bivalent avirulent Salmonella strains requires that the avirulent microorganism persist in the gut-associated lymphoid tissue (GALT or Peyer's patches) of the immunized individual for a period of time. Continuous production of the colonization and/or virulence antigen specified by genes from another pathogen is required to elicit a high level of protective immunity against the pathogen. Previous studies using traditional expression vectors with antibiotic resistance markers showed that most avirulent Salmonella isolated from immunized animals had, by one week, lost the recombinant plasmid encoding the immunizing antigen, and therefore were no longer able to elicit protective immunity against the pathogen. The use of an avirulent strain of Salmonella containing a delta-asd mutation and an expression vector containing the S. mutans or S. typhimurium asd$^+$ gene ensures stable maintenance of the cloned genes. In this regard, Chi4072 with pYA262 colonizes the GALT in Balb c mice so that titers of $10^4$ to $10^5$ SpaA producing cells are maintained one week after oral immunization. These titers are equivalent to those obtained with S. typhimurium Chi4064 (the asd$^+$ delta-cya delta-crp parent of Chi4072, see Table 1). The occasional lysis of a cell which has lost the asd$^+$ containing vector is beneficial since it releases the desired antigen, and thus augments the immune response against that antigen.

The production of a great diversity of commercially valuable by-products synthesized by genetically-engineered microorganisms has been achieved in the biotechnology industry. Stable maintenance of the genetically engineered microorganisms under fermenter growth conditions would be facilitated by the use of the cells of the invention, such as those containing delta-asd mutations and polynucleotide inserts into the same cell which carry an asd$^+$ gene as a selectable marker. The only cells which can grow and express proteins are those which encode the desired antigen. Thus, the yield of the desired product is increased.

The cells of the invention are also useful as microorganisms which can be released into the environment to destroy environmental pollutants, to eradicate insect pests, or to provide some benefit to plant species. In all cases, the invention creates cells in which viability is linked to expression of a desired cloned gene product.

I claim:

1. A live bacterial carrier for a vaccine for immunizing an individual, said carrier comprising an avirulent derivative of a pathogenic strain of bacteria characterized by:

a) a lack of a functioning native chromosomal gene encoding a first enzyme which is a β-aspartic semialdehyde dehydrogenase (Asd);

b) the presence of a first recombinant gene encoding a second Asd enzyme wherein the first recombinant gene cannot recombine to replace the defective chromosomal gene;

c) the presence of a second recombinant gene encoding a desired polypeptide; and d) physical linkage between the first recombinant gene and the second recombinant gene, wherein loss of the first recombinant gene causes the bacteria to lyse when in an environment which requires expression of said first recombinant gene for cell survival.

2. The live bacterial carrier according to claim 1 wherein said bacterial carrier is formulated in a pharmaceutically acceptable excipient in a pharmacologically effective dose.

3. The live bacterial carrier of claim 1, wherein the avirulent derivative of a pathogenic strain of bacteria is a Salmonella.

4. The live bacterial carrier of claim 3, wherein the first recombinant gene encodes Asd derived from *Streptococcus mutans*.

5. The live bacterial carrier of claim 4, wherein the second recombinant gene encodes an antigenic determinant encoded with the spaA gene of S. mutans.

6. The live bacterial carrier of claim 5, wherein the first recombinant gene encodes Asd derived from S. typhimurium.

7. A composition for stimulating an immune response in an individual comprising a live avirulent derivative of a pathogenic strain of bacteria characterized by:

a) a lack of a functioning native chromosomal gene encoding a first enzyme which is a β-aspartic semialdehyde dehydrogenase (Asd);

b) the presence of a first recombinant gene encoding a second Asd enzyme wherein the first recombinant gene cannot recombine to replace the defective chromosomal gene;

c) the presence of a second recombinant gene encoding a desired polypeptide; and physical linkage between the first recombinant gene and the second recombinant gene, wherein loss of the first recombinant gene causes the bacteria to lyse when in an environment which requires expression of said first recombinant gene for cell survival.

8. The composition of claim 7, wherein the avirulent derivative of a pathogenic strain of bacteria is a Salmonella.

9. The composition of claim 8, wherein the first recombinant gene encodes Asd derived from S. mutans.

10. The composition of claim 9, wherein the second recombinant gene encodes an antigenic determinant encoded within a spaA gene of S. mutans.

11. The composition of claim 10, wherein the first recombinant gene encodes Asd dervied from S. typhimurium.

12. A method of immunizing an individual comprising administering the live bacterial carrier for a vaccine of claim 1 to the individual.

13. A method of stimulating the immune system of an individual comprising administering the composition of claim 7 to the individual.

14. A method of preparing a bacterial carrier for a vaccine for immunization of an individual, said method comprising:

a) providing an avirulent derivative of a pathogenic strain of bacteria characterized by:
   1) a lack of a functioning native chromosomal gene encoding a first enzyme which is a β-aspartic semialdehyde dehydrogenase (Asd)
   2) the presence of a first recombinant gene encoding a second Asd enzyme wherein the first recombinant gene cannot recombine to replace the defective chromosomal gene;
   3)